(12) United States Patent
Ausk et al.

(10) Patent No.: US 10,835,689 B2
(45) Date of Patent: Nov. 17, 2020

(54) METHODS FOR INHIBITING HETEROTOPIC OSSIFICATION

(71) Applicant: University of Washington, Seattle, WA (US)

(72) Inventors: Brandon J. Ausk, Seattle, WA (US); Steven Bain, Seattle, WA (US); Ted S. Gross, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 484 days.

(21) Appl. No.: 15/634,927

(22) Filed: Jun. 27, 2017

(65) Prior Publication Data
US 2017/0290992 A1    Oct. 12, 2017

Related U.S. Application Data

(63) Continuation-in-part of application No. PCT/US2016/012761, filed on Jan. 8, 2016.
(Continued)

(51) Int. Cl.
*A61M 5/32* (2006.01)
*A61M 5/42* (2006.01)
(Continued)

(52) U.S. Cl.
CPC ....... *A61M 5/3297* (2013.01); *A61B 17/3403* (2013.01); *A61M 5/007* (2013.01);
(Continued)

(58) Field of Classification Search
CPC ........ A61M 5/46; A61M 5/20; A61M 5/3287; A61M 5/3295; A61M 5/00; A61M 5/19;
(Continued)

(56) References Cited

U.S. PATENT DOCUMENTS

2005/0137525 A1   6/2005 Wang et al.
2007/0055179 A1   3/2007 Deem et al.
(Continued)

FOREIGN PATENT DOCUMENTS

| WO | 9423777 | 10/1994 |
|---|---|---|
| WO | 2005039489 | 5/2005 |
| WO | 2016112361 | 7/2016 |

OTHER PUBLICATIONS

Seyler et al., "Botulinum Neurotoxin as a Therapeutic Modality in Orthopedic Surgery: More than Twenty Years of Experience", 2008, J Bone Joint Surg Am., 90:133-145 (Year: 2008).*
(Continued)

*Primary Examiner* — Kevin C Sirmons
*Assistant Examiner* — Alexandra Lalonde
(74) *Attorney, Agent, or Firm* — Kilpatrick Townsend & Stockton LLP

(57) ABSTRACT

Methods of protecting muscle tissue from heterotopic ossification employ targeted deliveries of a neuromuscular inhibitor. A method of protecting muscle tissue from heterotopic ossification includes identifying a volume of muscle tissue that is susceptible to heterotopic ossification. A first aliquot of a therapeutic dose of a neuromuscular inhibitor is delivered at a first delivery site within the volume of muscle tissue. A second aliquot of the therapeutic dose is delivered at a second delivery site within the volume of muscle tissue. The first and second delivery sites are separated by a distance to distribute the therapeutic dose within the targeted volume of muscle tissue.

19 Claims, 24 Drawing Sheets

Related U.S. Application Data

(60) Provisional application No. 62/101,089, filed on Jan. 8, 2015.

(51) Int. Cl.

| | |
|---|---|
| *A61B 17/34* | (2006.01) |
| *A61M 5/00* | (2006.01) |
| *A61M 5/19* | (2006.01) |
| *A61M 5/20* | (2006.01) |
| *A61M 5/315* | (2006.01) |
| *A61M 5/46* | (2006.01) |
| *A61B 17/20* | (2006.01) |

(52) U.S. Cl.
CPC ............... *A61M 5/19* (2013.01); *A61M 5/20* (2013.01); *A61M 5/31596* (2013.01); *A61M 5/427* (2013.01); *A61M 5/46* (2013.01); *A61B 17/205* (2013.01); *A61B 2017/3411* (2013.01); *A61M 5/3287* (2013.01); *A61M 5/3295* (2013.01); *A61M 2205/50* (2013.01); *A61M 2205/502* (2013.01); *A61M 2205/52* (2013.01)

(58) Field of Classification Search
CPC ............... A61M 5/31; A61M 5/31596; A61M 2005/1787; A61M 2202/0468; A61M 2210/08; A61M 2210/083; A61M 2210/086; A61B 17/3403; A61B 2017/3411; A61K 38/4893
See application file for complete search history.

(56) References Cited

U.S. PATENT DOCUMENTS

| | | | |
|---|---|---|---|
| 2007/0088348 | A1 | 4/2007 | Kochamba et al. |
| 2007/0260201 | A1 | 11/2007 | Prausnitz et al. |
| 2007/0276320 | A1 | 11/2007 | Wall et al. |
| 2009/0118662 | A1 | 5/2009 | Schnall et al. |
| 2009/0299328 | A1* | 12/2009 | Mudd .................. A61M 5/19 604/506 |
| 2010/0185177 | A1 | 7/2010 | Gillum et al. |
| 2012/0277156 | A1* | 11/2012 | Gross .................. A61K 31/167 514/16.7 |
| 2013/0345671 | A1 | 12/2013 | Ryu et al. |

OTHER PUBLICATIONS

International Search Report and Written Opinion dated Jun. 6, 2016, for corresponding PCT/US2016/012761 filed Jan. 8, 2016, 10 pages.
Aliprantis et al., "Transient Muscle Paralysis Degrades Bone via Rapid Osteoclastogenesis", FASEB J., vol. 26, No. 3, Mar. 2012, pp. 1110-1118.
Atmaca et al., "The Relation Between Botulinum Toxin-A and Fracture Healing. Comment on Hao et al.: Short-term Muscle Atrophy Caused by Botulinum Toxin-A Local Injection Impairs Fracture Healing in the Rat Femur", Journal of Orthopaedic Research, vol. 31, Mar. 2013, p. 510.
Ausk et al., "Cortical Bone Resorption Following Muscle Paralysis is Spatially Heterogeneous", Bone, vol. 50, No. 1, Jan. 2012, pp. 14-22.
Ausk et al., "Metaphyseal and Diaphyseal Bone Loss in the Tibia Following Transient Muscle Paralysis are Spatiotemporally Distinct Resorption Events", Bone, vol. 57, No. 2, Dec. 2013, pp. 1-23.
Aydin et al., "Effects of Botulinum Toxin a on Fracture Healing in Rats: An Experimental Study", Journal of Orthopaedic Science, vol. 17, No. 6, Nov. 2012, pp. 796-801.
Bain, "Transient Muscle Paralysis Inhibits Formation of Heterotopic Bone", University of Washington Orthopaedics and Sports Medicine, 2011, 5 pages.
Baird et al., "Prophylaxis of Heterotopic Ossification—an Updated Review", J. Orthop. Surg. Res., vol. 4, Apr. 20, 2009, 8 pages.
Bouxsein et al., "Guidelines for Assessment of Bone Microstructure in Rodents Using Micro-computed Tomography", Journal of Bone and Mineral Research, vol. 25, No. 7, Jul. 2010, pp. 1468-1486.
Cipriano et al., "Heterotopic Ossification Following Traumatic Brain Injury and Spinal Cord Injury", The Journal of the American Academy of Orthopaedic Surgeons, vol. 17, No. 11, Nov. 2009, pp. 689-697.
Feldman et al., "Over-expression of BMP4 and BMP5 in a Child with Axial Skeletal Malformations and Heterotopic Ossification: A New Syndrome", American Journal of Medical Genetics Part A, vol. 143A, No. 7, Apr. 1, 2007, pp. 699-706.
Firoozabadi et al., "Risk Factors for the Development of Heterotopic Ossification After Acetabular Fracture Fixation", Clinical Orthopaedics and Related Research, vol. 472, vol. 11, Nov. 2014, pp. 3383-3388.
Forsberg et al., "Heterotopic Ossification in High-Energy Wartime Extremity Injuries: Prevalence and Risk Factors", The Journal of bone and joint surgery, vol. 91, No. 5, May 2009, pp. 1084-1091.
Foruria et al., "Heterotopic Ossification After Surgery for Fractures and Fracture-Dislocations Involving the Proximal Aspect of the Radius or Ulna", The Journal of bone and joint surgery, vol. 95, No. 10, e66, May 15, 2013, pp. 1-7.
Garland et al., "A Clinical Perspective on Common Forms of Acquired Heterotopic Ossification", Clin. Orthop. Relat. Res., No. 263, Feb. 1991, pp. 13-29.
Garland et al., "Periarticular Heterotopic Ossification in Head-injured Adults. Incidence and Location", J. Bone Joint Surg. Am., vol. 62, No. 7, Oct. 1980, pp. 1143-1146.
Glass et al., "TNF-α Promotes Fracture Repair by Augmenting the Recruitment and Differentiation of Muscle-derived Stromal Cells", Proceedings of the National Academy of Sciences, vol. 108, vol. 4, Jan. 25, 2011, pp. 1585-1590.
Gross et al., "Muscle Function is Critical for Successful Fracture Healing", 54th Annual Meeting of the Orthopaedic Research Society, Poster No. 984, 2008, 1 page.
Hao et al., "Short-term Muscle Atrophy Caused by Botulinum Toxin-a Local Injection Impairs Fracture Healing in the Rat Femur", Journal of Orthopaedic Research, vol. 30, No. 4, Apr. 2012, pp. 574-580.
Hendricks et al., "Brain Injury Severity and Autonomic Dysregulation Accurately Predict Heterotopic Ossification in Patients with Traumatic Brain Injury", Clinical Rehabilitation, vol. 21, No. 6, Jun. 2007, pp. 545-553.
Kan et al., "Transgenic Mice Overexpressing BMP4 Develop a Fibrodysplasia Ossificans Progressiva (FOP)-like Phenotype", The American Journal of Pathology, vol. 165, No. 4, Oct. 2004, pp. 1107-1115.
Liu et al., "The Potential Role of Muscle in Bone Repair", J Musculoskelet Neuronal Interact, vol. 10, No. 1, Mar. 2010, pp. 71-76.
Lounev et al., "Identification of Progenitor Cells That Contribute to Heterotopic Skeletogenesis", The Journal of Bone and Joint Surgery (American), vol. 91, No. 3, Mar. 1, 2009, pp. 652-663.
Mummert et al., "Role of Transient Muscle Paralysis on the Development of Heterotopic Ossification", Journal of Undergraduate Research in Bioengineering, vol. 8, 2010, pp. 120-125.
Orzel et al., "Heterotopic Bone Formation: Clinical, Laboratory, and Imaging Correlation", J. Nucl. Med., vol. 26, No. 2, Feb. 1985, pp. 125-132.
Papakostidis et al., "Prevalence of Complications of Open Tibial Shaft Fractures Stratified as Per the Gustilo-Anderson Classification", Injury, vol. 42, No. 12, Dec. 2011, pp. 1408-1415.
Park, "Letter Regarding "Effects of Botulinum Toxin a on Fracture Healing in Rats: an Experimental Study"", Journal of Orthopaedic Science: Official Journal of the Japanese Orthopaedic Association, vol. 17, No. 6, Nov. 2012, 2 pages.
Poliachik et al., "Significant Trabecular Bone Degradation Occurs Within Five Days of Muscle Paralysis", J. Bone Min. Res., vol. 23, No. S1, 2008, p. 18-23.
Poliachik et al., "Transient Muscle Paralysis Disrupts Bone Homeostasis by Rapid Degradation of Bone Morphology", Bone, vol. 46, No. 1, Jan. 2010, pp. 18-23.

(56) References Cited

OTHER PUBLICATIONS

Potter et al., "Heterotopic Ossification Following Traumatic and Combat-Related Amputations. Prevalence, Risk Factors, and Preliminary Results of Excision", The Journal of Bone and Joint Surgery, vol. 89, No. 3, Mar. 2007, pp. 476-486.

Prasad et al., "Characterizing Gait Induced Normal Strains in a Murine Tibia Cortical Bone Defect Model", Journal of Biomechanics, vol. 43, No. 14, Oct. 19, 2010, pp. 2765-2770.

Regard et al., "Activation of Hedgehog Signaling by Loss of Gnas Causes Heterotopic Ossification", Nature Medicine, vol. 19, No. 11, Nov. 2013, pp. 1505-1512.

Salisbury et al., "Sensory Nerve Induced Inflammation Contributes to Heterotopic Ossification", J Cell Biochem., vol. 112, No. 10, Oct. 2011, pp. 48-58.

Sazbon et al., "Widespread Periarticular New-bone Formation in Long-term Comatose Patients", J. Bone. Joint Surg. Br., vol. 63-B, No. 1, Feb. 1981, pp. 120-125.

Shah et al., "The Role of Muscle in Bone Repair: The Cells, Signals, and Tissue Responses to Injury", Current Osteoporosis Reports, vol. 11, No. 2, Jun. 2013, pp. 130-135.

Stauber et al., "Micro-computed Tomography: a Method for the Non-destructive Evaluation of the Three-dimensional Structure of Biological Specimens", Methods Molecular Biology, vol. 455, 2008, pp. 273-292.

Strauss et al., "Cost of Radiotherapy Versus NSAID Administration for Prevention of Heterotopic Ossification After Total Hip Arthroplasty", Int. J. Radiat. Oncol. Biol. Phys., vol. 71, No. 5, Aug. 1, 2008, pp. 1460-1464.

Tippets et al., "Incidence of Heterotopic Ossification in Direct Anterior Total Hip Arthroplasty: a Retrospective Radiographic Review", The Journal of Arthroplasty, vol. 29, No. 9, Sep. 2014, pp. 1835-1838.

Warner et al., "Botox Induced Muscle Paralysis Rapidly Degrades Bone", Bone, vol. 38, No. 2, Feb. 2006, pp. 257-264.

\* cited by examiner

Saline-Treated

BTxA-Treated

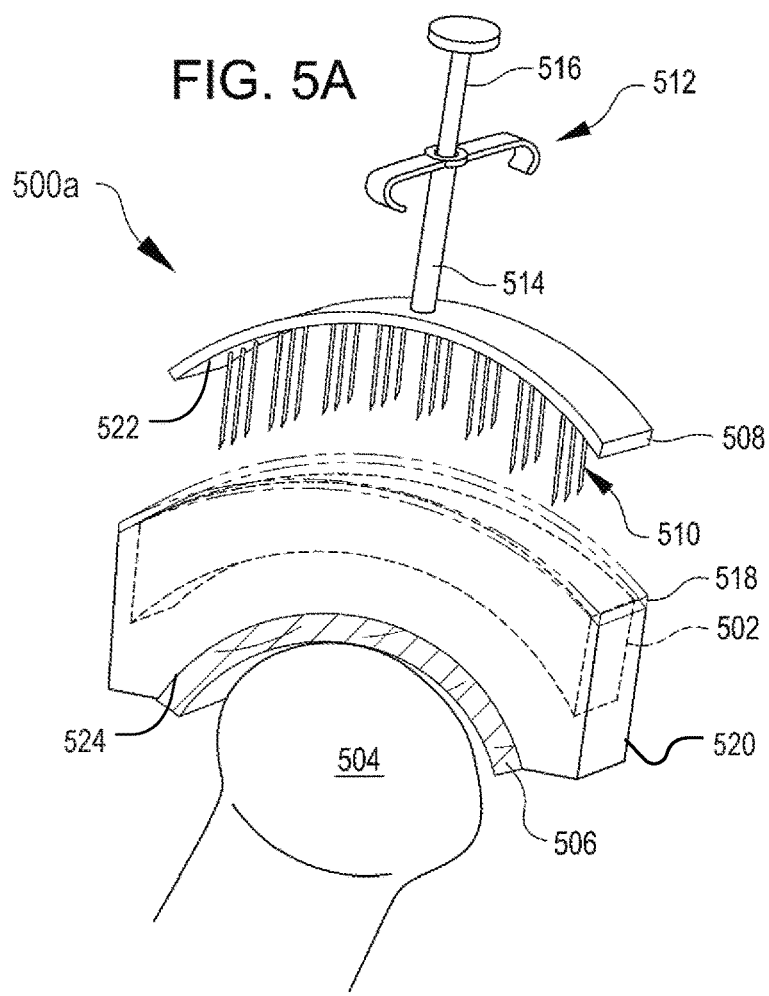
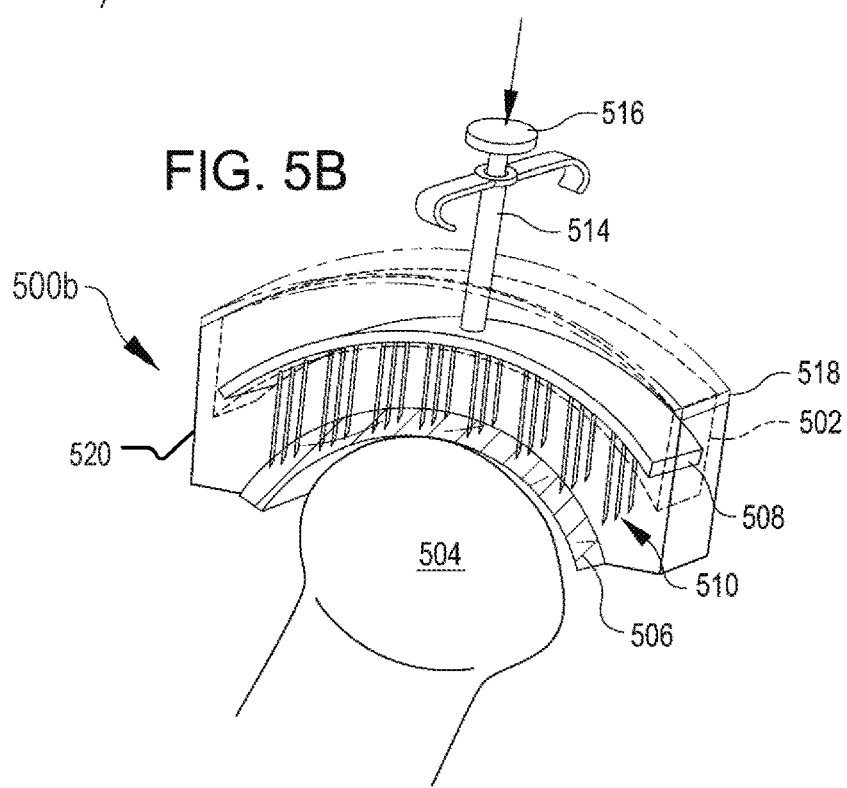

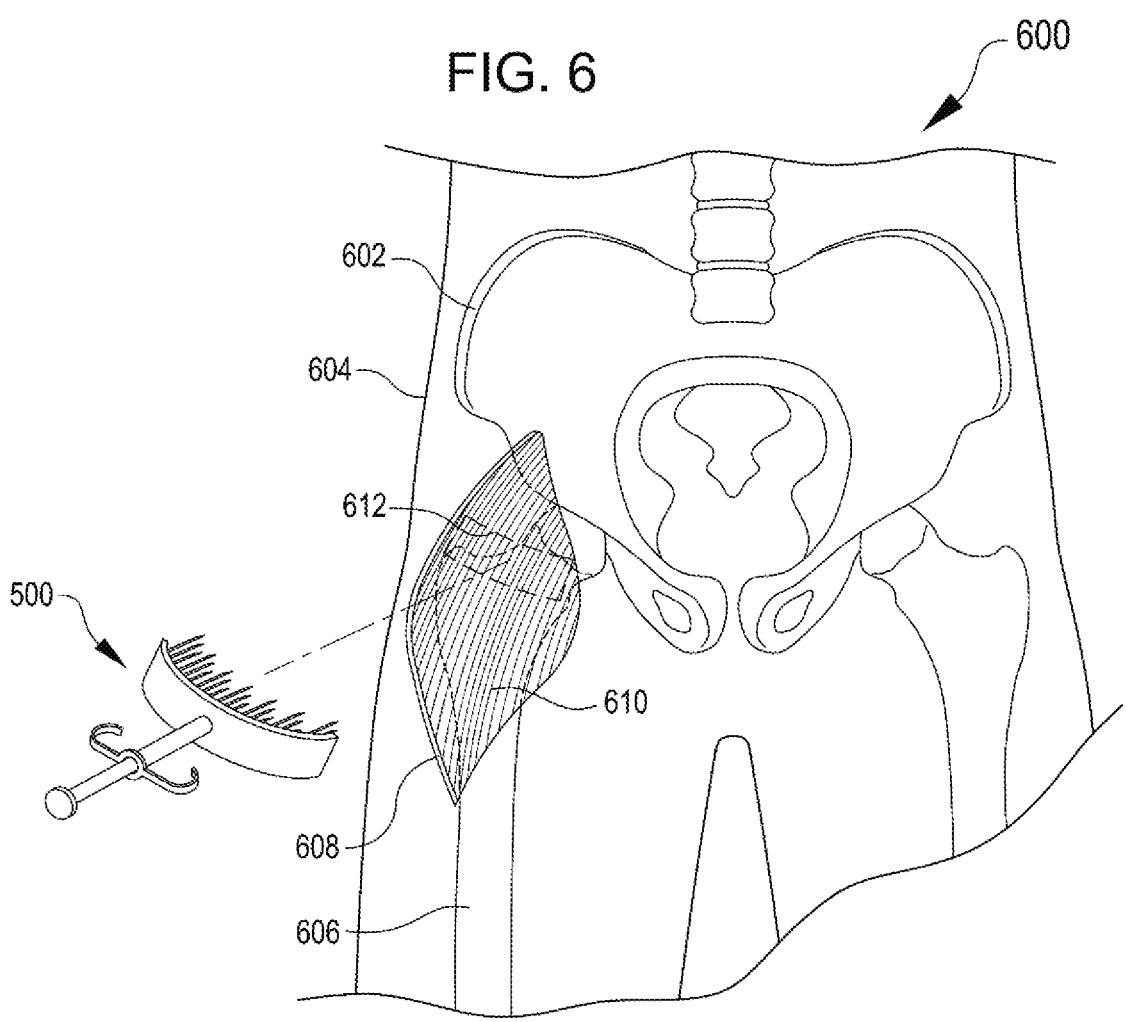

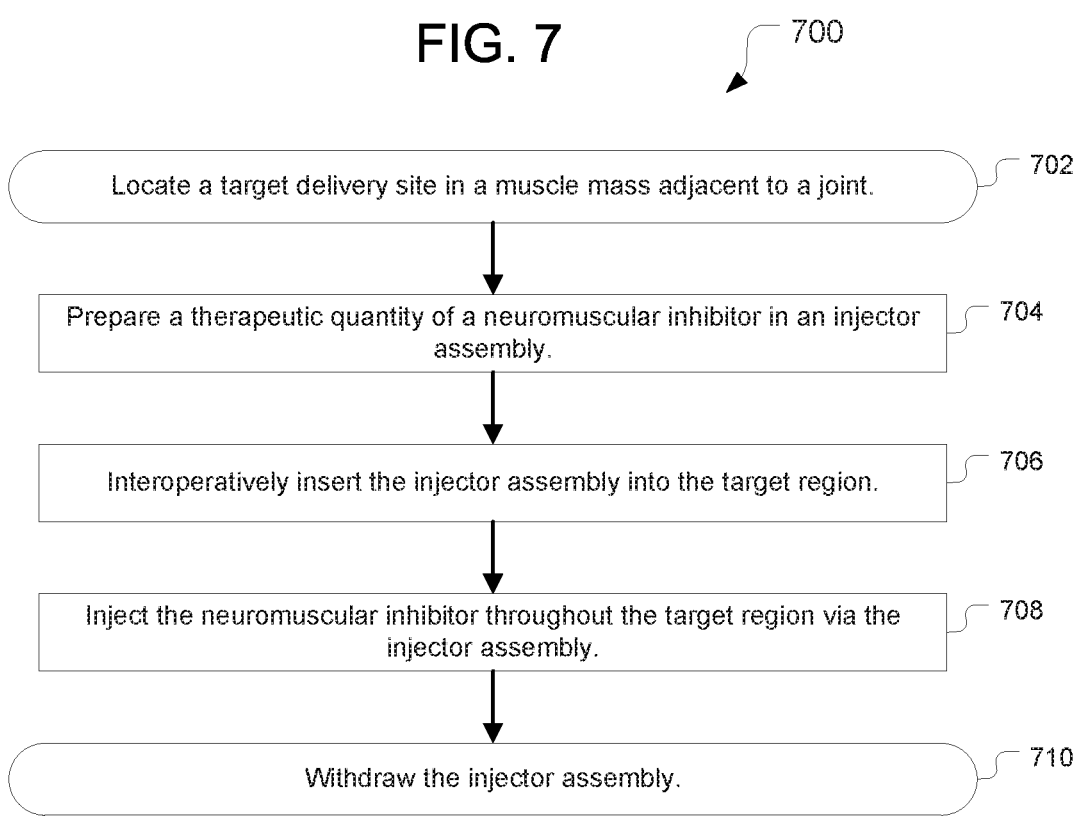

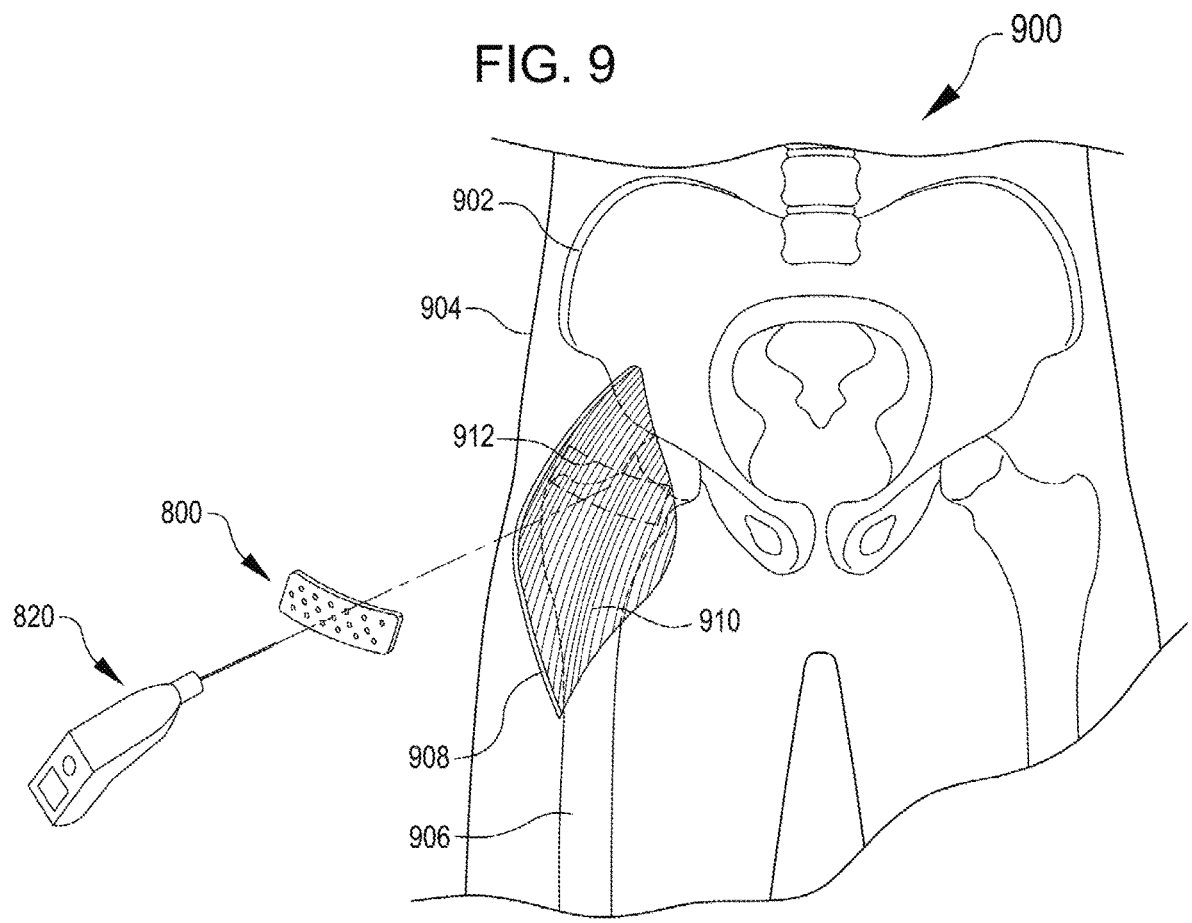

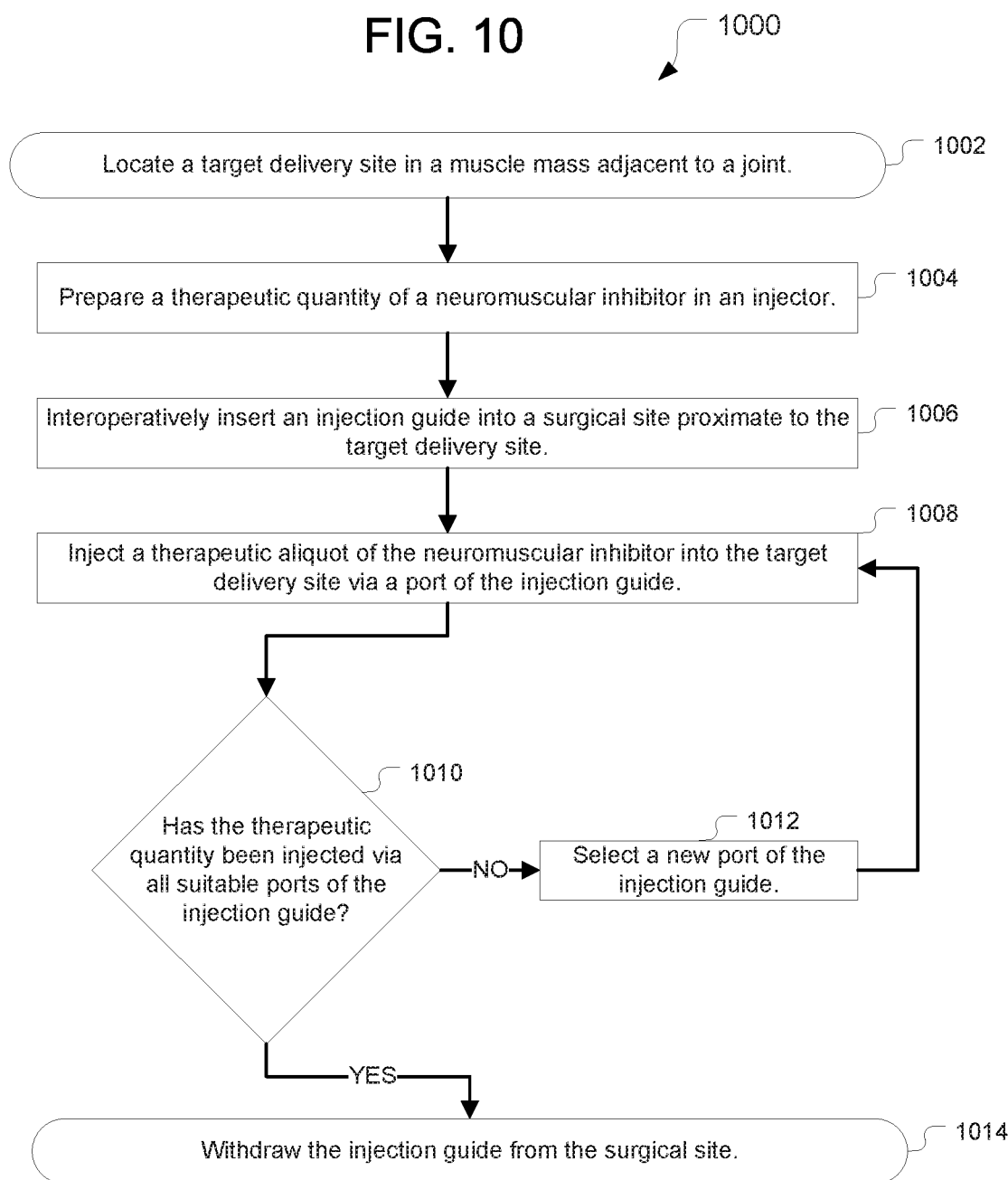

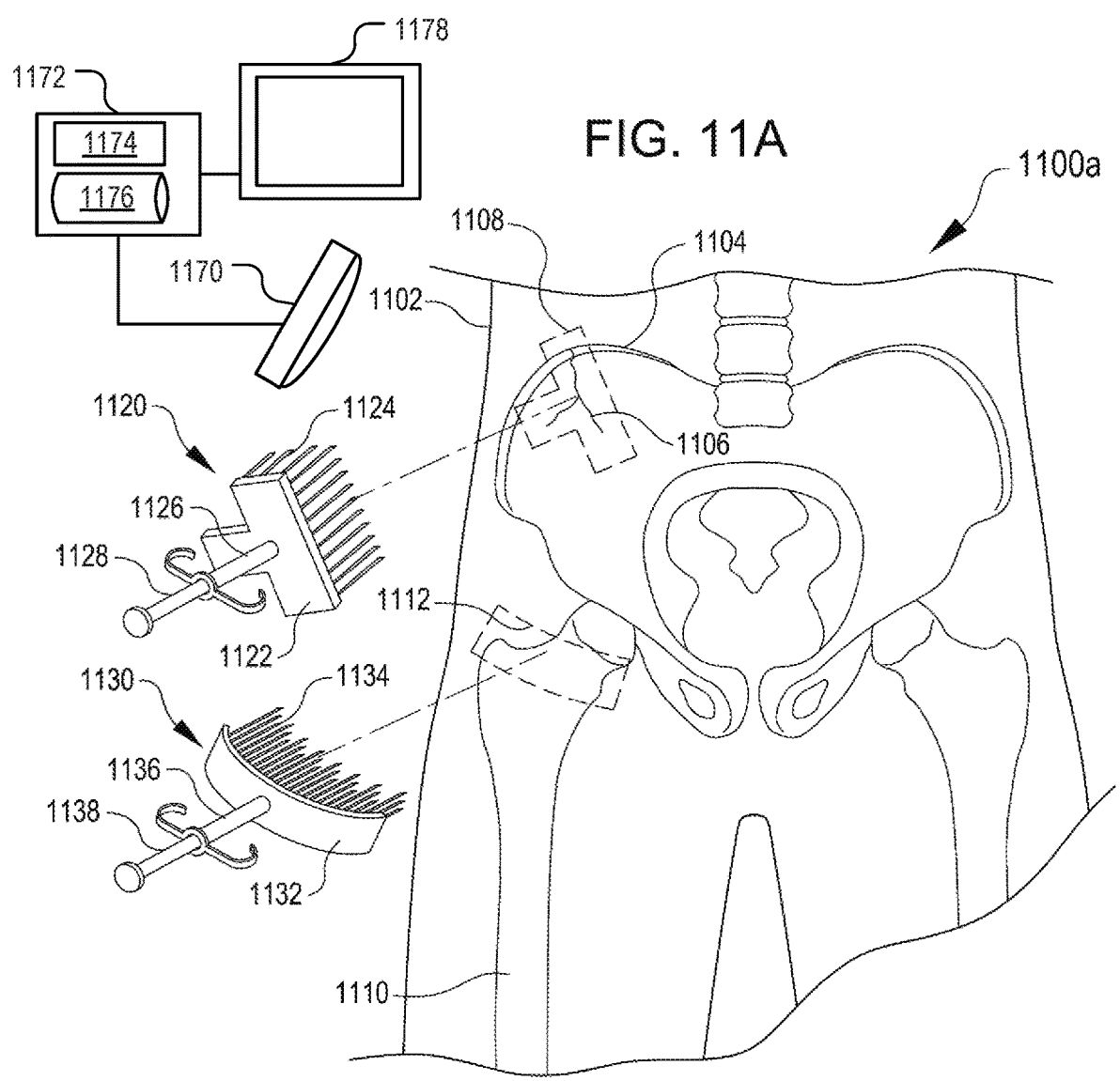

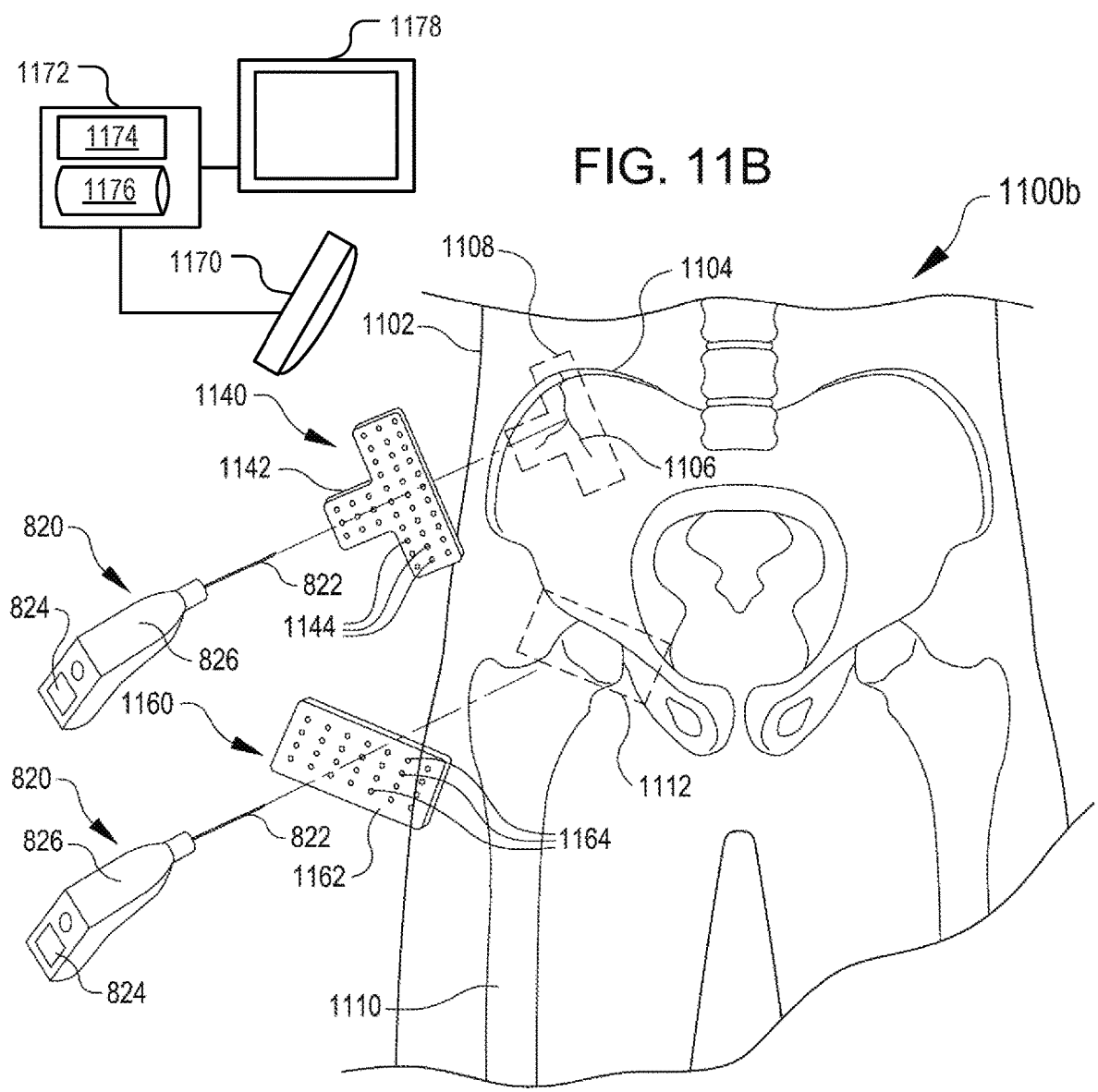

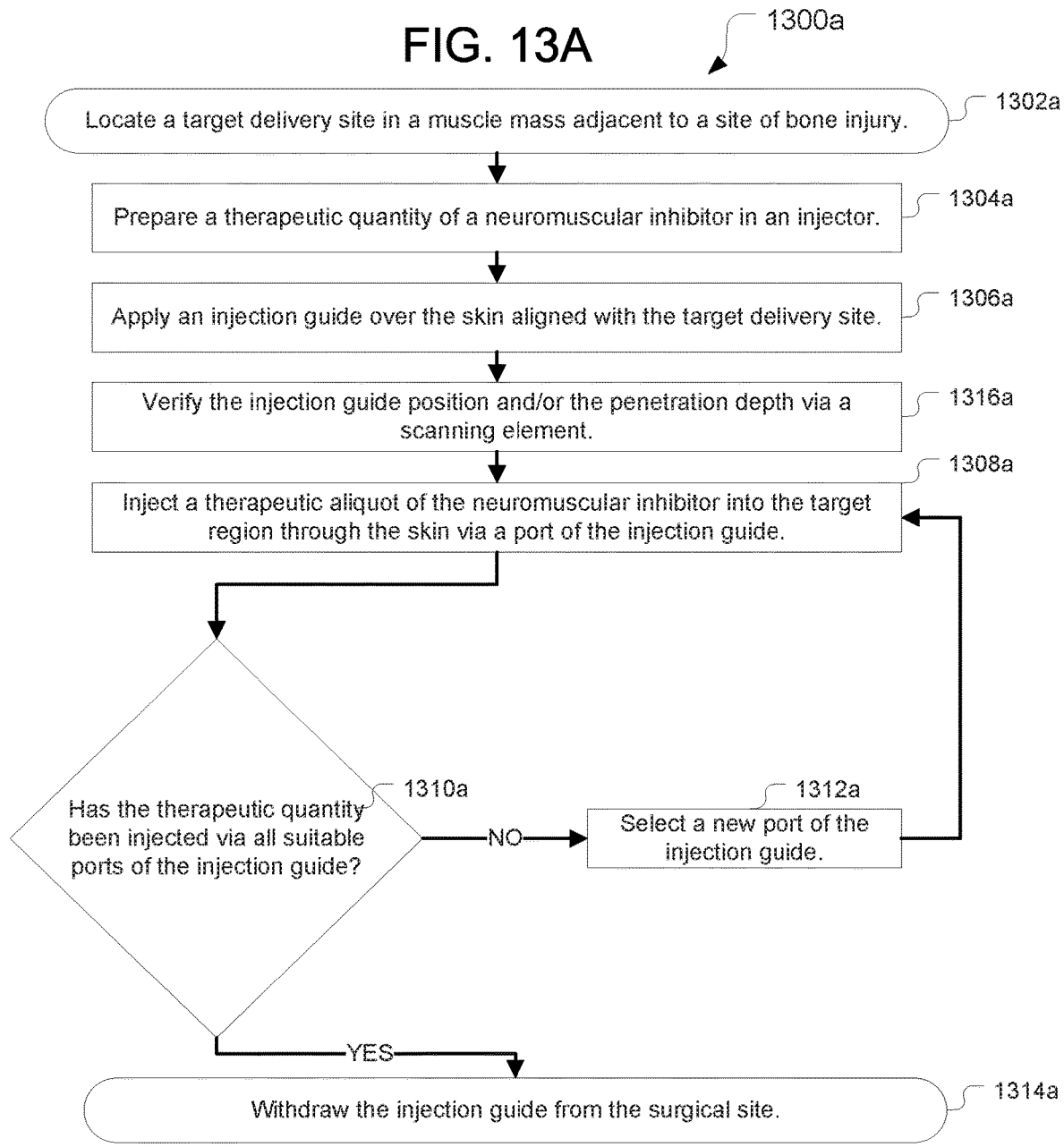

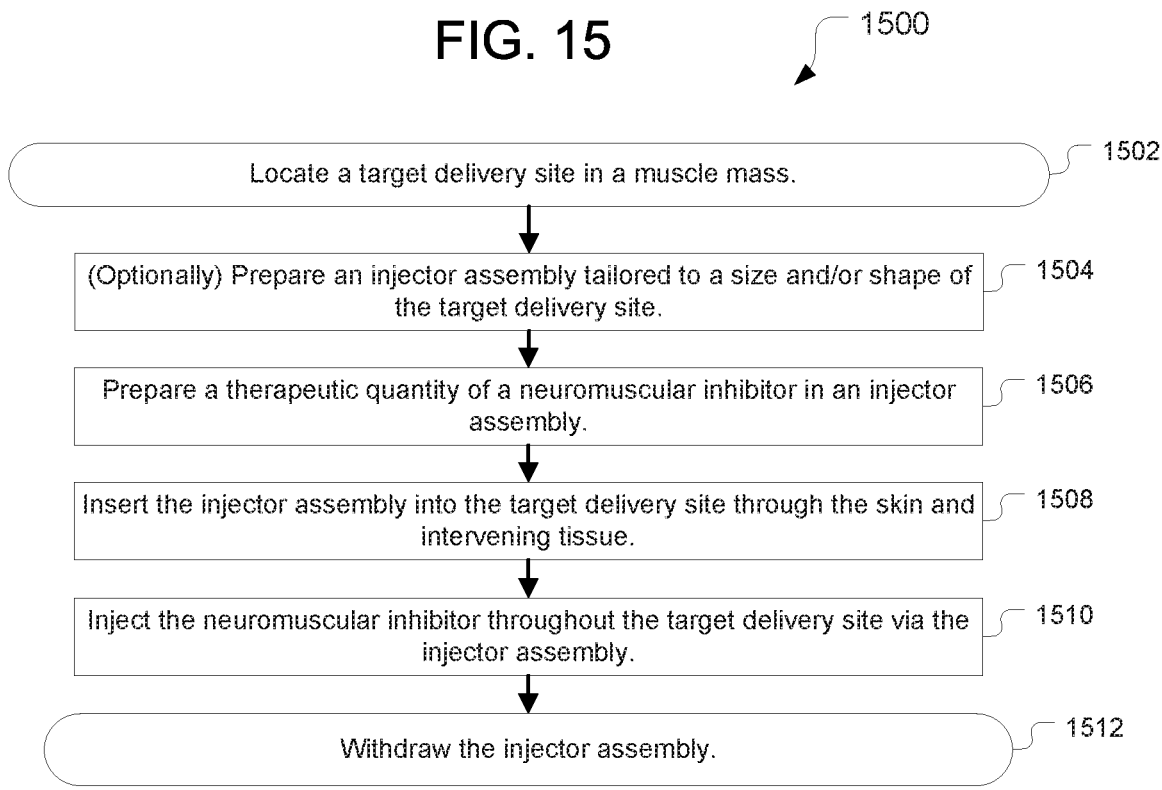

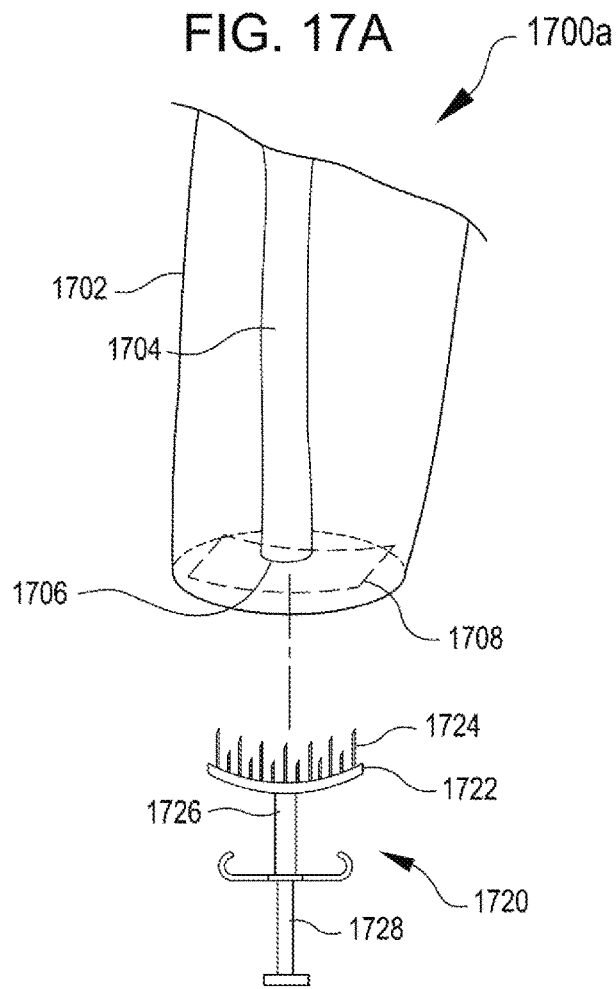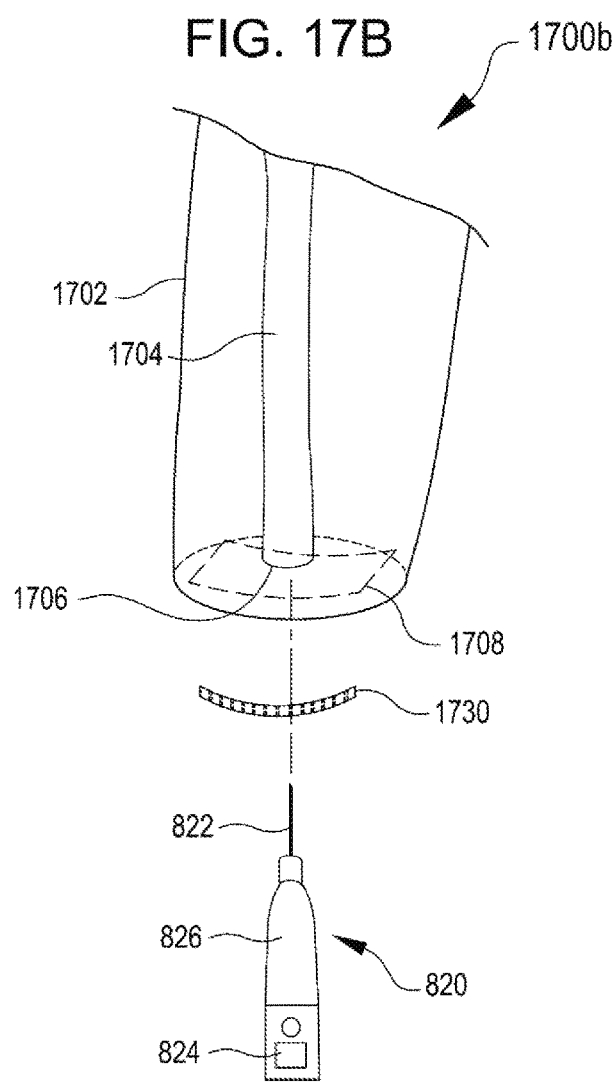

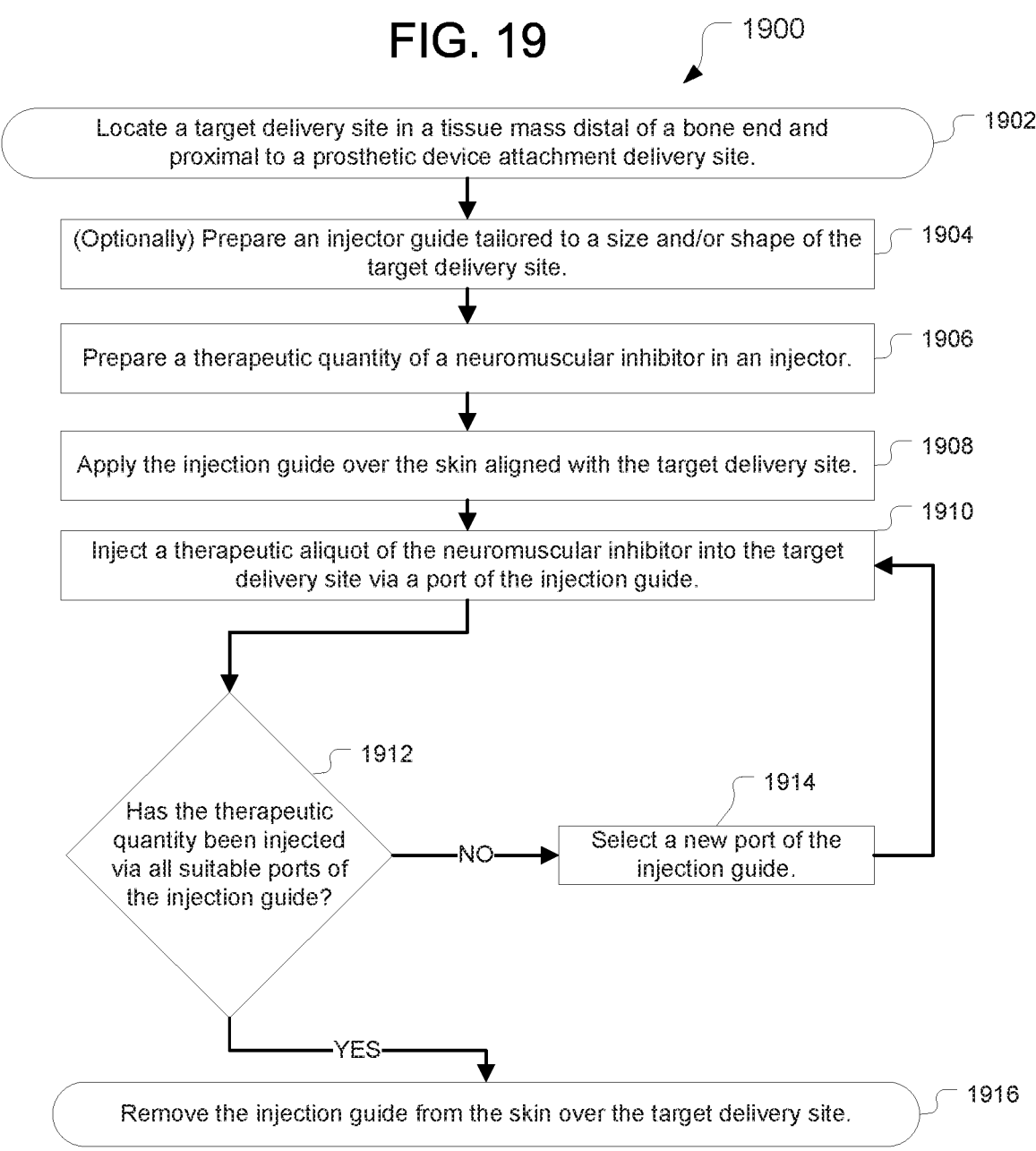

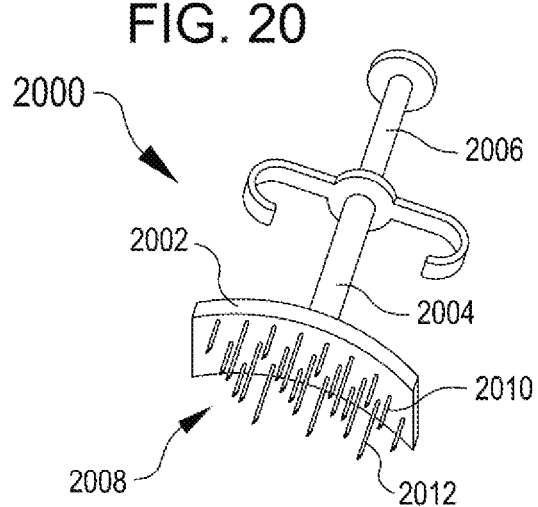
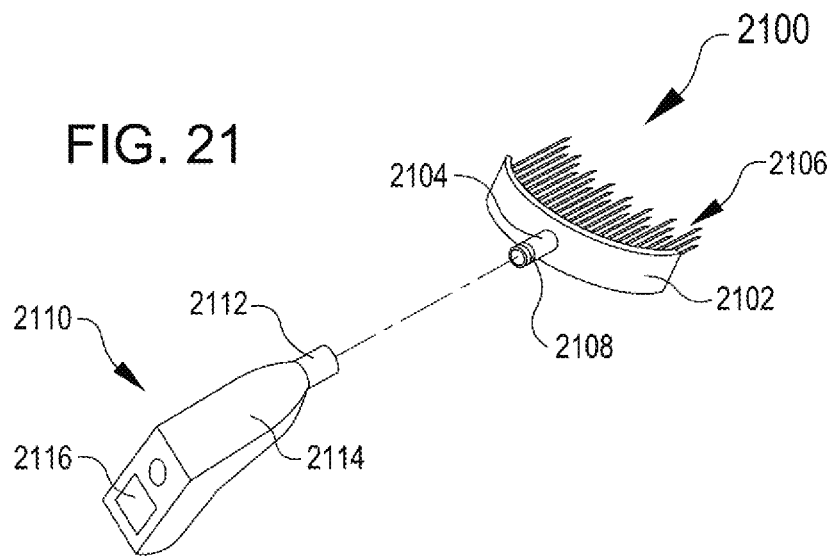

METHODS FOR INHIBITING HETEROTOPIC OSSIFICATION

CROSS-REFERENCE TO RELATED APPLICATIONS

The present application is a Continuation-in-Part of PCT/US2016/012761 filed Jan. 8, 2016; which claims priority to U.S. Provisional Application No. 62/101,089 filed Jan. 8, 2015, the disclosures of which are incorporated herein by reference in their entirety for all purposes.

Also incorporated by reference are previously filed applications: U.S. Ser. No. 13/386,043 filed Mar. 9, 2012, entitled INHIBITION OF PATHOLOGICAL BONE FORMATION; PCT/US2010/042741 filed Jul. 21, 2010; and Provisional Appln. No. 61/227,168 filed Jul. 21, 2009.

BACKGROUND

Heterotopic ossification ("HO") is the extra-skeletal formation of mature lamellar bone in soft tissue. HO is a potential complication of a number of different injuries, medical conditions, disorders, or the like, including, for example, spinal cord injuries, traumatic brain injuries, burns, fractures, muscle contusions, joint arthroplasty, amputation following trauma, lower motor neuron disorders, hereditary disorders, or the like or combinations thereof. At least one study has shown that the incidence of HO for these conditions ranges from 11% to 76%, depending on the population studied and the method of diagnosis. HO may result in joint contracture and ankylosis, severe pain, spasticity, swelling, fever, neurovascular compression, lymphedema, pressure ulcers, and significant disability, most commonly around proximal limb joints.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Various embodiments herein described relate to apparatuses, systems, and methods for inhibiting the formation of a heterotopic ossification lesion (an "HO lesion.") In many embodiments, a therapeutic agent is administered in a therapeutically-effective distributed manner. In many embodiments, the therapeutic agent is distributed within a target muscle region susceptible to HO lesion formation. By prophylactically administering a therapeutic agent to the HO susceptible region in a therapeutically-effective distributed manner, the likelihood of subsequent formation a HO lesion in the HO susceptible region is substantially reduced.

Thus, in one aspect, a delivery device can include an injector having a shaped surface configured for complimenting a shape of a target delivery location of a patient. The shaped surface can be further connected with an array of needles. The needles are arranged to pierce the target delivery location and operably connected with the injector such that the needles can distribute a therapeutic agent to the target delivery location. In some cases, the delivery device can be an assembly including a delivery device body that receives the injector and array of needles, such that the device body can space the shaped surface away from the target delivery location of the patient, in order to achieve a target depth of penetration such that the needle ends come to rest in a correct volume of the target delivery location when the delivery device is applied to the patient.

In another aspect, a delivery device can include an injector guide having a shaped surface configured for complimenting a shape of a target delivery location of a patient, and having an array of voids or holes for accommodating a needle of a syringe or injector. In some cases, the injector guide can be used in conjunction with a device body as described above. In some cases, an injector can include needles at multiple lengths, such that distal ends of the needles can project to various depths when the injector is inserted in a target delivery location. In some cases, an injector guide can have depressions at multiple depths around voids or holes, such that a distal end of an injector needle can project to various depths when the injector is inserted in a target delivery location.

In another aspect, a method of treatment of heterotopic ossification can include identifying a target delivery location in a patient, e.g. a selected volume of tissue, for a therapeutic dose of a HO inhibiting agent. The target delivery location may be a volume of muscle tissue susceptible to the formation of heterotopic ossification lesions. In some cases, the target delivery location may be a volume of muscle tissue proximate to a joint, and particularly in a region impinged by flexure of the joint, within which the formation of a heterotopic ossification lesion might impede joint flexure. The method can further include delivering a first aliquot of the HO inhibiting agent at a delivery site within the volume, and delivering a second aliquot of the HO inhibiting agent at another delivery site within the volume. In some cases, the method can include delivering aliquots of the HO inhibiting agent distributed throughout the volume of the target delivery location, so as to ensure that the HO inhibiting agent is distributed evenly in the volume.

In another aspect, a system for treating, i.e. mitigating or preventing, heterotopic ossification can include a delivery device, such as one of the delivery devices described above. The delivery device can be assembled with a reservoir containing a therapeutic quantity of a neuromuscular inhibitor, and with an ejection means fluidly connected with the reservoir. The system can be configured to eject aliquots of the therapeutic quantity into a volume of the target delivery location. In some cases, the system can include a medical imaging system for correctly locating the injector in the delivery volume.

In another aspect, a system for treating, i.e. mitigating or preventing, heterotopic ossification can include an injection guide system for interacting with an injection means such as an automatic injector or comparable device. According to some embodiments, the injection guide system can include a guide element (i.e. a base guide element) and one or more additional guide elements. The additional guide elements can include matching features for aligning and/or connecting with the base guide element, as well as an array of holes or ports therethrough that align with holes or ports in the base guide element. In operation, the additional guide elements can be used to selectively modify the total thickness of a guide element stack including the base guide element, to enable a user to inject at multiple discrete depths in a repeatable pattern through the guide element stack by placing or removing the additional guide elements. According to some other embodiments, the injection guide system can include a guide element and one or more spacers. The spacers can be attached with a needle of an automatic injector or other suitable injection means, and may be stacked in series to create a spacer stack. The spacer stack can be used to selectively modify the effective length of the needle. When used in conjunction with a guide element, the needle and spacer stack enable a user to inject at multiple discrete depths in a repeatable pattern through the spacer stack by placing or removing spacers, and by injecting at selected holes or ports in the guide element. According to some alternative embodiments, spacers and additional guide elements may be used in combination to achieve various injection patterns.

For a fuller understanding of the nature and advantages of the present invention, reference should be made to the ensuing detailed description and accompanying drawings.

BRIEF DESCRIPTION OF THE DRAWINGS

Various embodiments in accordance with the present disclosure will be described with reference to the drawings, in which:

FIG. 5A illustrates a delivery device for distributed injection of an HO inhibiting agent in a region of tissue in a pre-injection configuration, according to embodiments;

FIG. 5B illustrates the delivery device of FIG. 5A in an injection configuration;

FIG. 6 illustrates intraoperative treatment of an acetabular region using a delivery device to distribute an HO inhibiting agent, according to embodiments;

FIG. 7 illustrates a process for performing an intraoperative treatment of a region of muscle adjacent to a joint, according to embodiments;

FIG. 9 illustrates intraoperative treatment of a muscle mass adjacent to a joint using an injection guide and an automatic injector to inhibit HO formation, according to embodiments;

FIG. 10 illustrates a process for performing an intraoperative treatment of a muscle mass adjacent to a joint, according to embodiments;

FIG. 11A illustrates protective treatment of the acetabular region to inhibit HO formation in conjunction with a mitigating treatment of the iliac region to inhibit HO formation, using injector assemblies, according to embodiments;

FIG. 11B illustrates protective treatment of the acetabular region to inhibit HO formation in conjunction with a mitigating treatment of the iliac region to inhibit HO formation, using injection guides and an automatic injector, according to embodiments;

FIG. 13A illustrates a process for performing treatment of a muscle mass adjacent to a bone injury using an injection guide and an automatic injector to inhibit HO formation, according to embodiments;

FIG. 15 illustrates a process for performing a protective treatment of a muscle mass using a delivery device to inhibit HO formation, in accordance with embodiments;

FIG. 17A illustrates protective treatment of an amputated limb using a delivery device to inhibit HO formation, in accordance with embodiments;

FIG. 17B illustrates protective treatment of an amputated limb using an injection guide and an automatic injector to inhibit HO formation, in accordance with embodiments;

FIG. 19 illustrates a process for performing a protective treatment of an amputated limb using an injection guide and an automatic injector to inhibit HO formation, according to embodiments;

FIG. 20 illustrates a delivery device having needles at varying lengths for distributing an HO inhibiting agent, according to embodiments;

FIG. 21 illustrates a delivery device assembly that is attachable with an automatic injector for use in distributing an HO inhibiting agent in a muscle mass, according to embodiments;

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

HO is a potential secondary complication of musculoskeletal trauma. Embodiments described herein are directed to inhibition of HO formation via distributed delivery of an HO inhibiting agent.

Two complementary small animal studies were performed using an accepted model of inducing HO via implantation of BMP-2 in a basement membrane carrier. The first study assessed the specific mechanism of HO inhibition via BTxA injection. In particular, the first study indicated that BTxA injection inhibits HO formation via local inhibition of neuromuscular function and not via the muscle paralysis or skeletal unloading that can be caused by said inhibition. Secondarily, the first study indicated that intervention to inhibit HO formation has a spatial limitation, i.e., HO will be inhibited within a finite distance from the injection site, depending on dose, volume, and the amount of diffusion. The second study demonstrated that separating a given dose into smaller volumes and injecting them at a distance from one another can reduce side effects of BTxA treatment without a corresponding loss of efficacy of inhibition of HO.

Figure 1A:
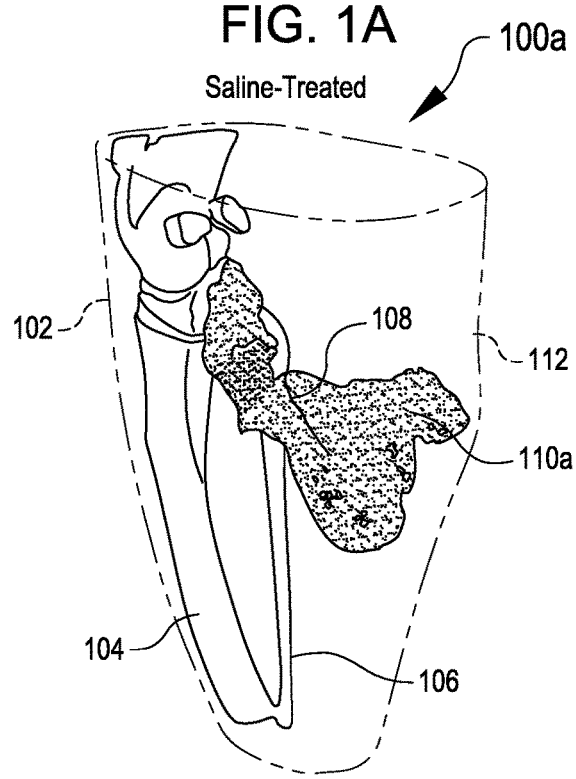
FIG. 1A is a schematic perspective view of an HO lesion that was surgically induced in a saline-solution treated calf of a mouse.

By way of example, FIG. 1A shows a first schematic perspective view 100a of an HO lesion based on a three-dimensional volumetric micro-CT reconstruction of a volume of a calf of a mouse, showing of saline-treated control. The regions illustrated include the anterior 102, tibia 104, fibula 106, the region associated with initial HO lesion formation 108, and the calf 112. An HO lesion 110a was triggered via implantation of BMP-2 in a basement membrane carrier into the calf 112, followed by a 20 µL injection of saline solution.

Figure 1B:
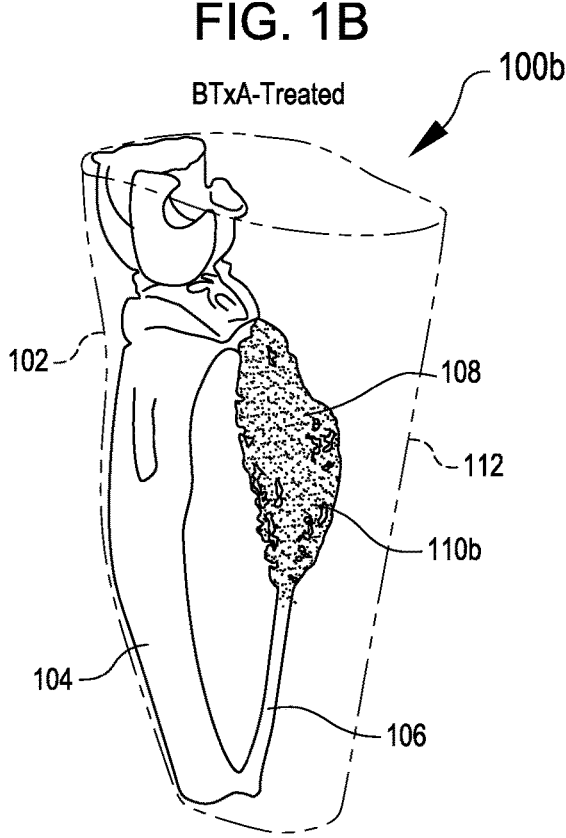
FIG. 1B is a schematic perspective view of an HO lesion that was surgically induced in a BTxA treated calf of a mouse.

FIG. 1B shows a second schematic perspective view of an HO lesion 100b based on a three-dimensional volumetric reconstruction of a volume of a calf of a mouse, showing a BTxA-controlled test. As described above, an HO lesion 110b has been induced via implantation of BMP-2 in a basement membrane carrier into the calf 112. In place of the saline solution, a BTxA injection (of 2.0 U/100 g body weight) was applied in a volume of 20 µL. The HO lesions 110a, 110b are markedly different in these two cases, with the untreated control lesion 110a forming a very large nodule, and the treated lesion 110b forming a much smaller and more localized lesion that does not significantly penetrate the volume of the calf 112.

Methods:

All animal procedures were performed using protocols and procedures approved by the Institutional Animal Care and Use Committee of the University of Washington. Female C57Bl/6 mice were obtained from Jackson Laboratories and were a mean age of 20.3 weeks when the below-described studies were initiated.

In each of the below-described studies, heterotopic bone formation was induced in the right calf muscle group through implantation of BMP-2 in a basement membrane carrier. On day 0 of the studies, implants were prepared by adding recombinant human BMP-2 (Syd Labs Inc., Natick, Mass.) to liquid Cultrex® basement membrane extract, PathClear® (BME; Trevigen®) at 4° C. All mice were anesthetized and their gastrocnemii were injected with BMP-2/BME solution (2.5 µg BMP-2/20 µl of BME). BMP-2/BME injection occurred at the midbelly of the gastrocnemius muscle (at a 45° angle from the muscle surface with the needle pointing proximally) inducing heterotopic lesions in the proximal calf muscle.

Twenty-four hours prior to BMP-2/BME implantation, muscle paralysis was achieved through targeted injection of botulinum neurotoxin A ("BTxA"). This time point was chosen to limit the potential for direct interactions between the BTxA and BMP-2/BME injections. Immediately prior to BTxA injection, mice were anesthetized with isoflurane and their right hind limb secured in a custom apparatus that allowed for reproducible positioning of the calf muscle, which exposed the predicted location of the HO lesion and insured accurate measurement and identification of BTxA injection sites. To achieve targeted injection location and precision dosing, a stereotaxic frame and digital microinjection system (UMP3 with NanoFil® syringes, WPI Inc., Sarasota, Fla.) was used to inject microliter amounts of BTxA perpendicular to the muscle surface at specific anatomical sites and depths. Percutaneous injection occurred at a subcutaneous depth of between 4-5 mm. As in all BTxA treated animals, calf muscle paralysis was confirmed 24 hours post-injection by visual examination of reduced toe extension and ankle plantar flexion in the affected limb.

Figure 2:
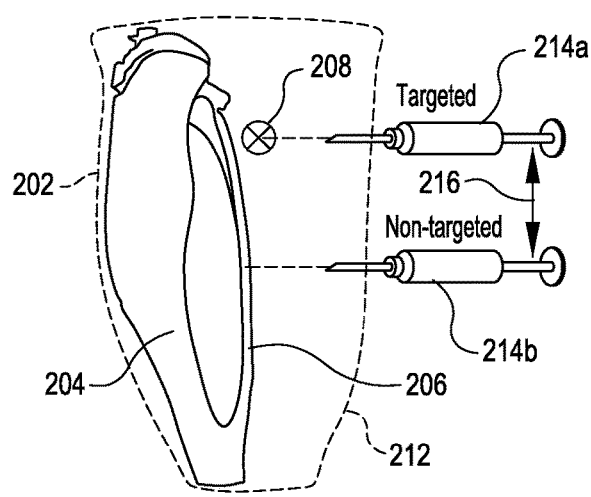
FIG. 2 illustrates the injection of a neuromuscular inhibitor into two different target delivery locations along a calf of a mouse.

First Study:

FIG. 2 illustrates aspects of the first study, examining the effect of targeted muscle paralysis on BMP-2 induced HO formation in a hind limb 200 of a mouse. Visible parts of the hind limb 200 include an anterior 202, tibia 204, fibula 206, and calf 212. HO lesion formation was induced via implantation of BMP-2 in a basement membrane carrier into the calf muscle groups 212. A region associated with initial HO lesion formation 208 is the target volume for injection of the targeted dose 214a. In this study, female C57 mice were randomized to: 1) BMP-2+Targeted saline; 2) BMP-2+Targeted BTxA; and 3) BMP-2+Non-targeted BTxA (n=6/grp). Anesthetized mice received calf injection in their right hind limbs of either 20 µl saline (Group 1) or BTxA (0.5 Units) in a volume of 20 µl (Group 2 and 3). In the targeted groups (Group 1 and 2), injection of the targeted dose 214a occurred at the midline of the proximal gastrocnemius at the predicted HO location (FIG. 2). In the Non-targeted group (Group 3), BTxA injection of the non-targeted dose 214b occurred 4 mm distal 216 of the predicted location of initial HO lesion formation 208.

Figure 3:
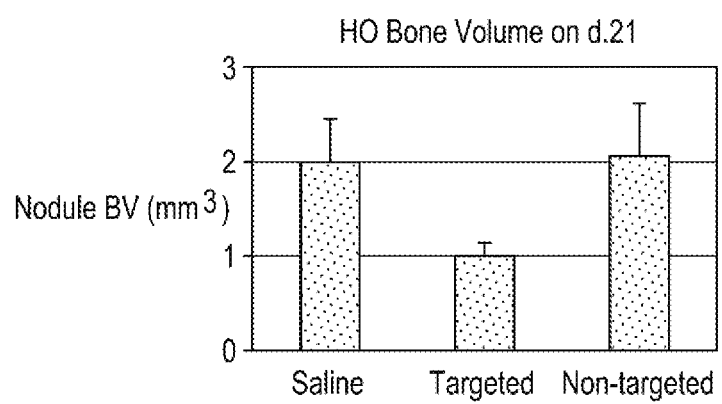
FIG. 3 is a graph of experimental data showing a relationship between HO lesion volume associated with a control (FIG. 1A), with BTxA administered at the site of the HO inducement (FIG. 2) and with BTxA administered away from the site of the HO inducement (FIG. 2)

First Study Results:

The results of the first study appear to indicate that there is a spatial relationship between neuromuscular inhibition and a reduction of heterotopic bone formation. In particular, the results showed that efficacy of treatment increased as the distance between the patient target delivery location and the region of anticipated heterotopic bone formation was reduced. Animals injected with BMP-2+saline had profound heterotopic bone formation in the proximal calf muscle group of the experimental limb (FIG. 3—Saline, 1.99±0.45 mm$^3$, mean±s.e.). When paralysis was targeted to the site of BMP injection, neuromuscular inhibition reduced the lesion bone volume by 50% (FIG. 3—Targeted, 1.00±0.12 mm$^3$). However, locating the BTxA injection just 4 mm distal within the same muscle group eliminated the inhibitory effect on the bone volume of the induced lesion (FIG. 3—Non-targeted, 2.06±0.57 mm$^3$). As all mice in the study demonstrated identical gait dysfunction commensurate with calf paralysis, muscle paralysis does not directly lead to inhibition of HO.

Second Study:

The second study explored whether altering dose or distributing a given total dose of a neuromuscular inhibitor into smaller spatially distributed doses (while maintaining the same total dose) would reduce negative musculoskeletal side-effects without a corresponding loss of HO volume reduction. In this study, female C57 mice were randomized to: 1) BMP-2+Targeted saline; 2) BMP-2+0.1 U Targeted BTxA; 3) BMP-2+0.5 U Targeted BTxA; and 4) BMP-2+0.5 U Targeted BTxA (in two half doses). All groups were injected using an identical setup to that described in the first study. Injections in Group 4 occurred 2 mm medial and lateral to the Targeted midline injection location (0.25 U BTxA in 10 µl per dose).

Figure 4A:
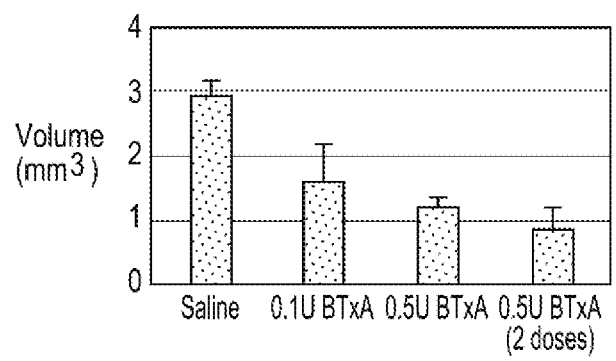
FIG. 4A is a graph of experimental data showing a relationship between different dosages and distributions of a neuromuscular inhibitor and volume of heterotopic bone formation.

Second Study Results:

The results of the second study demonstrate that inhibition of HO via BTxA injection is a function of dose and the distribution of that dose. As well, these data indicate that spatial distribution of a given dose into smaller doses (of equivalent total dose) improves efficacy of HO inhibition while reducing muscle atrophy and bone loss. For example, the second study demonstrated that the BTxA dose needed for reducing HO could be reduced at least 5-fold while still retaining efficacy. In particular, lowering the BTxA dose to 0.1 U retained significant efficacy as compared to 0.5 U (FIG. 4A-0.1 U BTxA, 1.62±0.53 mm$^3$).

Figure 4B:
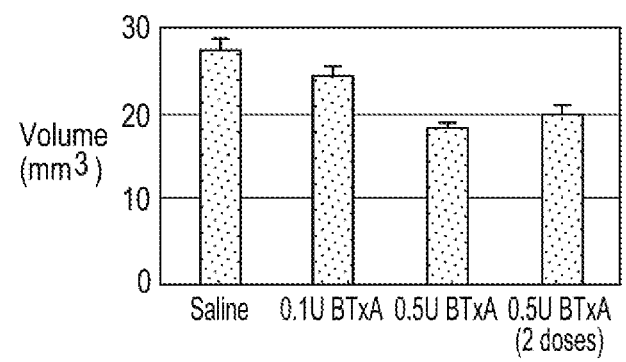
FIG. 4B is a graph of experimental data showing a relationship between different dosages and distributions of a neuromuscular inhibitor and calf muscle volume in proximity to heterotopic bone formation.
Figure 4C:
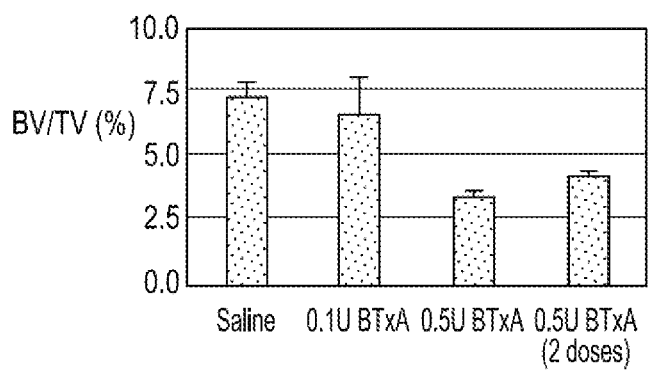
FIG. 4C is a graph of experimental data showing a relationship between different dosages and distributions of a neuromuscular inhibitor and volume of non-heterotopic tibia bone in proximity to heterotopic bone formation.

Moreover, the results appear to indicate that efficacy can be retained while simultaneously reducing muscle atrophy and bone loss, as compared to administration of higher doses of the neuromuscular inhibitor. The results indicate that profound ectopic bone formation was induced in animals injected with BMP-2+saline (FIG. 4A-Saline, 2.95±0.20 mm$^3$), while targeted treatment with 0.5 U BTxA reduced the lesion volume by 59% (FIG. 4A-0.5 U BTxA, 1.21±0.10 mm$^3$). However, this reduction in heterotopic bone volume was accompanied by a 32% reduction in calf muscle volume (FIG. 4B-Saline vs. 0.5 U BTxA, 27.41±1.02 vs. 18.51±0.01 mm$^3$) and a 53% reduction in bone volume fraction (BV/TV) within the proximal tibia metaphysis (FIG. 4C-Saline vs. 0.5 U BTxA, 7.36±0.54 vs. 3.44±0.14%). Lowering the BTxA dose to 0.1 U retained significant efficacy as compared to 0.5 U (FIG. 4A-0.1 U BTxA, 1.62±0.53 mm$^3$) and substantially reduced side effects, as compared to 0.5 U (64% muscle atrophy and 81% BV/TV loss, FIGS. 4B and 4C).

The results of the second study further indicate that administering a BTxA dosage in multiple injections may be preferential to administering the entire dosage in a single injection. For example, when 0.5 U of BTxA was targeted as two doses of 0.25 U (medial and lateral calf), the intervention was 12% more effective in inhibiting HO than a single 0.5 U mid-calf injection (FIG. 4A). The results also indicate that spatially distributing the BTxA was also more successful in mitigating muscle loss (FIG. 4B) and trabecular bone loss (FIG. 4C) than a single 0.5 U dose. Scaling of the BTxA dose required to inhibit HO in the mouse model suggests for human application a total cumulative dose range of between 10 U and 1200 U of BTxA within a 3-month period in order to produce similar results.

In both studies, µCT imaging was performed in all mice for 21 days following BMP-2 implantation to determine nodule bone volume (Scanco vivaCT 40; 21 µm voxel resolution). Mice were anesthetized and maintained on isoflurane and the right tibia was secured in a custom apparatus to maintain leg position during the scan process. µCT topogram (or "µCT scout") images were obtained to determine the location of the heterotopic lesion within the affected muscle. Based on topogram images, µCT scans originated from the tibiofibular junction and continued proximally until the entire HO lesion was imaged. Once scans were obtained, HO volumes were isolated using an automated contouring algorithm and a threshold of 480.7 mg HA/ccm was used to identify calcified tissue within the heterotopic nodule. Standard bone morphologic parameters were obtained in both studies. In the second study, calf muscle parameters and bone volume fraction in the proximal tibia metaphysis was also quantified as a measure of BTxA induced side effects. Prior to data analysis, one mouse was removed from the second study (Group 3) due to its heterotopic lesion fusing with the fibula, which prevented accurate quantification of HO morphology.

Device:

FIGS. 5A-5B show embodiments of a therapeutic-agent-delivery device 500a and 500b (cumulatively 500) ("device"), such as a neuromuscular-inhibitor-delivery device, configured and arranged to deliver one or more therapeutic agents, such as one or more neuromuscular inhibitors, to a target delivery location at, or in proximity to, a region of anticipated heterotopic bone formation. In some embodiments, the delivery device 500 may be used for intraoperative or percutaneous delivery of the therapeutic agent to a patient, e.g. a patient undergoing a surgical procedure such as a hip replacement. In particular, the delivery device 500 can be used to deliver the therapeutic agent throughout a target delivery location such that the delivery may be distributed sufficiently close to all portions of the targeted location to effectively inhibit HO lesion formation. In some embodiments, the distribution reduces a required dose size of a neuromuscular inhibitor such that HO lesion formation may be inhibited while minimally impacting overall muscle function, or such that muscle paralysis may be localized to the target region, thus mitigating muscle atrophy.

FIG. 5A shows an embodiment of a delivery device assembly 500a including an injector 512 and a device body 520, with the device body 520 being positioned adjacent to a delivery site 506 in a patient. The injector 512 is shown positioned above the device body 520. In some embodiments, the device body 520 can be seated at an injection site 506 prior to injection using the delivery device assembly 500a, and the injector 512 can subsequently be lowered into the device body 520 through an opening in the top 518 of the device body 520 and via an interior cavity 502 of the device body 520. In some embodiments, the top 518 of the device body may be a cover for preserving a sterile field and may be removed prior to assembling the injector 512 with the device body 520. The injector 512 can include an injector body 508 and an array of needles 510 fluidly connected with the injector body 508. In some embodiments, the array of needles 510 can be fluidly connected via the injector body 508 with a barrel 514 and plunger 516 for dispensing a therapeutic agent. In some embodiments, an ejection means other than a barrel and plunger might be used. For example, an automated injector or injector-control device, such as a computer-controlled dispenser, might be fluidly connected with the barrel 514 or injector body 508 in order to deliver a quantity of the therapeutic agent. The injector 512 can include a contact surface 522, which may be curved, and in some embodiments can be curved to match either or both of a curvature of the device body 520 and a body part of a patient. Likewise, the device body 520 can include a contact surface 524, which in some embodiments can be curved to match a body part of a patient.

Needles in the array of needles 510 can be spaced in any suitable shape of array, such as a square array, close-packed array, a heterogeneous distribution of needles, a distribution of needles having concentrated and sparse regions, or other suitable configuration. In various embodiments, needles can be spaced apart from each other at distances ranging from less than 4 mm to less than or equal to 50 mm. For example, in one distribution, a dose may be split between two large injections targeted to opposing sides of the femoral head, at approximately 50 mm. In some embodiments, more than two needles may be spaced such that adjacent needles in the array of needles 510 are approximately 20 mm apart.

FIG. 5B shows a delivery device assembly 500b including an injector body 520 assembled with the injector 512 (of FIG. 5A) and in position to deliver the therapeutic agent to the delivery site 506. The shape of the injector body 520 can adjust a protruding depth of the array of needles 510, such that the array of needles ends at the delivery site 506 without impinging on a region outside the delivery site, e.g., the bone 504 below the targeted tissue or clinically insignificant soft tissue volumes. In some embodiments, the interior cavity 502 of the device body 520 can be shaped to match the injector body 508. In some embodiments, both of the device body 520 and injector body 518 can be concave in the direction of the array of needles 510, so as to better interact with a delivery site 506 around a convex region such as a bone; but the exact shape and size of the device body 520 and the injector body 508 can be varied to accommodate a different delivery site, e.g. a delivery site with a more pronounced curvature, less pronounced curvature, or an inverted curvature. In some embodiments, the device body 520 may be customizable for an individual, e.g. made smaller for a patient of small stature or made larger for a patient of large stature; or may be customized depending on the particular portion of the body to which the treatment is applied. In some embodiments, the injector body 508 may be customizable as well.

In some embodiments, the delivery device assembly 500b may be assembled prior to use, such that the entire assembly 500b is applied as a whole, without first applying the device body 502, in which case the top 518 of the device body 520 can further include a cap, lid, filling, or other suitable structure for holding the injector body 508 in place within the interior cavity 502 of the device body 520. In some embodiments, the injector body 508 can be partially inserted into the interior cavity 502 of the device body 520, such that the delivery device assembly 500b can be handled as a single part, but such that the array of needles 510 does not extrude from the device body 520 until pressed into place by a user. The needle array 510 of the delivery device assemblies 500a, 500b may possess needles at spatial intervals configured to distribute the therapeutic agent throughout the volume of the delivery site 502. Furthermore, other embodiments of delivery device assemblies (500a, 500b) and injector bodies (508) can be used with or without a device body comparable to device body 520.

Embodiments of a delivery device assembly may be used for treatment of many different neuromuscular/musculoskeletal conditions (e.g., heterotopic ossification) that are treatable via site-specific, targeted delivery of one or more therapeutic agents (e.g., one or more neuromuscular inhibitors). By way of further example, FIGS. 6-19 illustrate aspects of additional systems and methods of site-specific treatment using neuromuscular inhibitors.

FIG. 6 diagrammatically illustrates a system 600 for intraoperative treatment of a delivery region 612 in the acetabular region for inhibiting HO formation using a delivery device 500, according to embodiments. In the intraoperative treatment 600 a surgical wound 608 has been opened proximate to the delivery region 612 for a procedure such as a hip joint replacement. Shown are approximate locations of the bones of the hip 602, the skin 604, the femur 606, and a muscle layer 610 passing over the joint of the hip and femur (the acetabular joint). The delivery device 500 (see also FIGS. 5A, 5B) can include an injector body 520 (as shown in injection device assembly 500b of FIG. 5B), can be inserted into an injector body or guide in the surgical wound 608 (see FIG. 5A), or can be inserted directly into the surgical wound 608 and positioned such that the needles of the delivery device 500 penetrate the delivery region 612.

FIG. 7 illustrates a process 700 for performing an intraoperative treatment of the acetabular region, as shown in FIG. 6, according to embodiments. In an embodiment, the process includes locating a target region in a muscle mass adjacent to a joint, e.g. the acetabulofemoral joint, and particularly a target region that is impinged by flexure of the joint (act 702). A therapeutic quantity of a neuromuscular inhibitor can be prepared in a delivery device assembly, for example the delivery device 500 (FIG. 6), based on, for example, dosing requirements for inhibition of HO formation, regulatory limitations on the dose size of various particular neuromuscular inhibitors, or other suitable factors (act 704). In intraoperative procedure, such as stage of a hip replacement, which in some embodiments may be a final stage prior to closing the surgical wound, the delivery device assembly can be inserted into the surgical wound so that the delivery device assembly penetrates a volume of the target region (act 706), and then the neuromuscular inhibitor can be injected into the volume of the target region via the delivery device assembly (act 708) before it is withdrawn (act 710).

Figure 8A:
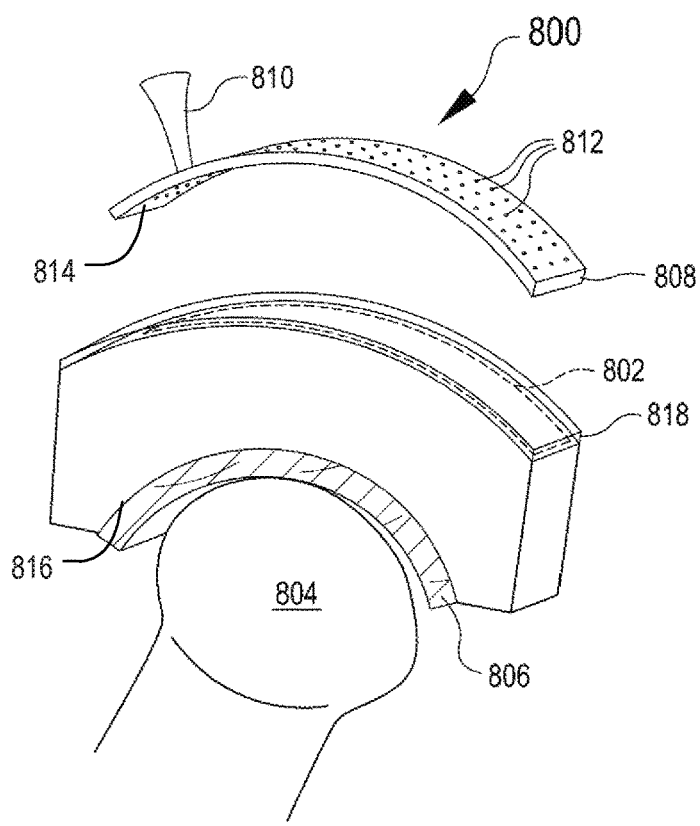
FIG. 8A illustrates an injection guide for distributing injection an HO inhibiting agent in a region of tissue in a pre-injection configuration, according to embodiments.

FIG. 8A illustrates an injection guide assembly 800 for injection of an HO inhibiting agent, such as a neuromuscular inhibitor. The injection guide assembly 800 can include a guide 808 and a device body 802 that receives the guide 808 in a receiving region 818 so as to form the guide assembly 800. The guide 808 includes a plurality of guide holes 812 configured to guide a needle, and may include holding features 810 for enhancing handling by a user. The device body 802 can be placed over a delivery site 806 in a patient, so that the combination of the guide 808 and the device body 802 controls the placement and the depth of injection through the guide holes 812, for example, to ensure that any therapeutic agent is delivered to the delivery site 806 and not too deep, i.e., at a bone 804 underlying the delivery site 806. The injection guide 808 can include a contact surface 814, which may be curved, and in some embodiments can be curved to match either or both of a curvature of the device body 802 and a body part of a patient. Likewise, the device body 802 can include a contact surface 816, which in some embodiments can be curved to match a body part of a patient.

Figure 8B:
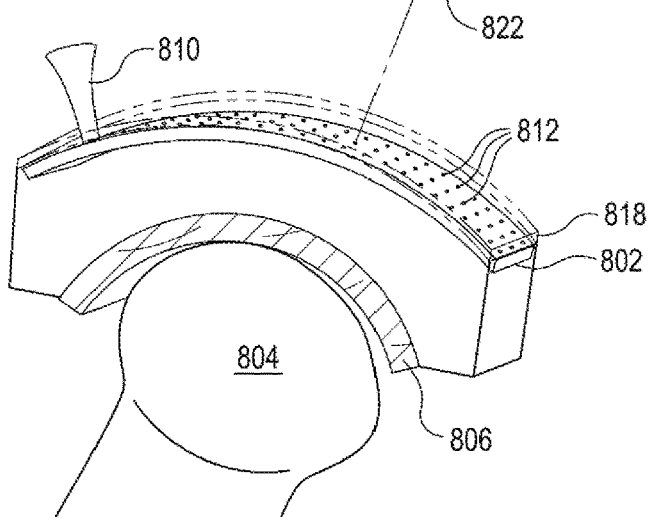
FIG. 8B illustrates the injection guide of FIG. 8A in an injection configuration for distributing injection of an HO inhibiting agent with an automatic injector, according to embodiments.

FIG. 8B illustrates the injection guide assembly 800 of FIG. 8A, with the guide 808 and device body 802 assembled together, in the injection position, with an automatic injector 820, according to embodiments. The automatic injector 820 can include an injection needle 822, a device body 826, and controls 824, and can contain a therapeutic quantity of the therapeutic agent for delivery to the delivery site 806. The automatic injector can be further configured to aliquot the therapeutic quantity according to a number of discrete injections based on the volume of the delivery site 806, such that the therapeutic quantity is delivered over a series of injections through the guide holes or injection guide ports 812. It is understood that said aliquots may be of equal or unequal volumes at each point of injection. In some embodiments, the series of injections can include injecting using the entire set of guide holes 812; but in some embodiments, a subset of the guide holes can be used according to a medical need, such as a smaller volume of the delivery site 806.

In some embodiments, the injection guide assembly 800 can be used with a different form of injector than the automatic injector 820. For example, manual injection can be performed through the injection guide assembly 800 using one or more conventional syringes. In some embodiments, the injection guide 808 can be used in the absence of a device body 802. For example, the injection guide 808 can be any suitable thickness for modifying an effective length of the needle 822 of the automatic injector 820, so as to reduce a number of parts of the assembly. In some embodiments, the injection guide 808 and device body 802 can be combined prior to application to a patient. Furthermore, in some embodiments, the injection guide 808 can be used directly on a patient in the absence of an additional device body, such as when the injection guide 808 may be applied directly to the skin of a patient with a layer of intervening tissue between the guide 808 and the delivery site 806. Alternatively, in some embodiments, a user may apply the guide 808 to the skin or intraoperatively, and ensure a correct depth by gauging the depth of penetration of the needle 822 during a procedure, or by modifying the needle 822 (e.g., with a sleeve) so as to restrict a depth of penetration.

FIG. 9 diagrammatically illustrates a system 900 for intraoperative treatment of a delivery region 912 in the acetabular region for inhibiting HO formation using an injection guide assembly 800 (FIGS. 8A-8B), according to embodiments. In the intraoperative treatment 900 a surgical wound 908 has been opened proximate to the delivery region 912 for a procedure such as a hip joint replacement. Shown are approximate locations of the bones of the hip 902, the skin 904, the femur 906, and a muscle layer 910 passing over the joint of the hip and femur (the acetabular joint). The injection guide assembly 800 can include an injection guide 808 (as shown in injection device assembly 800 of FIG. 8A) with or without a device body 802, and can be inserted into a device body 802 in the surgical wound 908, or can be inserted directly into the surgical wound 908, and can be positioned such that the needles of an automatic injector 820 (or other suitable injection means) penetrate the delivery region 912 by passing through the injection guide assembly 800.

FIG. 10 illustrates a process 1000 for performing an intraoperative treatment of the acetabular region, as shown in FIG. 9, according to embodiments. In an embodiment, the process includes locating a target region in a muscle mass adjacent to a joint, e.g. the acetabulofemoral joint, and particularly a target region that is impinged by flexure of the joint (act 1002). A therapeutic quantity of a neuromuscular inhibitor can be prepared in an injector, such as the automatic injector 820 (FIGS. 8B-9), based on, for example, dosing requirements for inhibition of HO formation, regulatory limitations on the dose size of various particular neuromuscular inhibitors, or other suitable factors (act 1004). In an intraoperative procedure, such as stage of a hip replacement, which in some embodiments may be a final stage prior to closing the surgical wound, the injector can be inserted into the surgical wound via the injection guide so that a needle of the injector penetrates a volume of the target region (act 1006), and then a therapeutic aliquot of the neuromuscular inhibitor can be injected into a portion of the volume of the target region via the injector (act 1008). As long as the therapeutic quantity has not yet been injected into all suitable holes or ports of the injection guide (act 1010), a new port can be selected for injection (act 1012) and injection of therapeutic aliquots via the injection guide (act 1008) can be repeated. When the therapeutic quantity has been exhausted and/or has been injected through all suitable ports of the injection guide (1010), the injection guide can be withdrawn from the surgical site (act 1014).

The examples above describe intraoperative delivery of an therapeutic agent for purposes of preventing HO formation in a region associated with joint flexure, in conjunction with a surgical procedure such as a hip replacement. In embodiments, procedures like the above can mitigate or prevent HO formation in regions where the presence of HO lesions would impact patient ambulation. However, in various embodiments, a therapeutic agent can be delivered through the skin as well as intraoperatively, or can be delivered to a different site than a region associated with joint flexure. For example, delivery can be targeted to a region that is associated with the formation of an HO lesion based on trauma to a nearby bone; or in the absence of a known site of likely HO lesion formation, delivery can be targeted to a region surrounding or proximate to the site of trauma, such as limb amputations and/or around a residual limb/prosthetic interface.

FIG. 11A diagrammatically illustrates a system 1100a for protective percutaneous treatments of the acetabular region for preventing HO formation, including a mitigating treatment of a trauma site and a treatment proximate to the acetabulofemoral joint for inhibiting HO formation, using injector assemblies applied through the skin, according to embodiments. Shown are approximate locations of the skin 1102, the bones of the hip 1104, the femur 1110, and an example of a fracture 1106 in the iliac region of the hip 1104.

In a mitigating treatment proximate to the site of the trauma, a first delivery site 1108 can be chosen to approximate the area of intended protection from HO formation. A first delivery device assembly 1120 can be prepared with an injector 1122. In some cases, the delivery device assembly 1120 may be sized and/or shaped to match the first delivery site 1108. The delivery device assembly 1120 can include an injector 1122, an array of needles 1124, and a barrel 1126 sized to fit a plunger 1128 in order to transfer a therapeutic agent into the delivery site 1108 via the array of needles 1124. In some embodiments, the delivery device assembly 1120 can be used in conjunction with a device body similar to the device body 520 (FIGS. 5A, 5B) to modify a depth of penetration of the array of needles 1124 in order to match a depth of the delivery site 1108.

In a mitigating treatment proximate to a joint near the trauma 1106, a second delivery site 1112 can be chosen, which in the present example can be a target region in a muscle mass adjacent to the acetabulofemoral joint, and particularly a region that is impinged by flexure of the joint. A second delivery device assembly 1130 can be prepared with an injector 1132. In some embodiments, the second delivery device assembly 1130 may be sized and/or shaped to match the second delivery site 1112. The delivery device assembly 1130 can include an array of needles 1134, and a barrel 1136 sized to fit a plunger 1138 in order to transfer a therapeutic agent into the delivery site 1112 via the array of needles 1134. In some embodiments, the delivery device assembly 1130 can be used in conjunction with a device body similar to the device body 520 (FIGS. 5A, 5B) to modify a depth of penetration of the array of needles 1134 in order to match a depth of the delivery site 1112.

A scanning element 1170 can be applied in conjunction with either delivery device assembly 1120, 1130 for scanning one or both of the first and second delivery sites 1108, 1112, e.g., for determining the correct depth of penetration (for customizing or adjusting the injector assemblies 1120, 1130), or during a procedure to verify the position of one or both arrays of needles 1112, 1134. The scanning element 1170, which can include an ultrasound device, MM device, X-Ray device, or other suitable medical scanner, can be operably connected with a computer system 1172 having a processor and memory 1174, 1176 configured to image and display the scanned region at a display 1178.

FIG. 11B diagrammatically illustrates a system 1100b for protective percutaneous treatment of the acetabular region for preventing HO formation, including a mitigating treatment of a trauma site and a treatment proximate to the acetabulofemoral joint for inhibiting HO formation, using injection guides and an automatic injector applied through the skin, according to embodiments. Shown are approximate locations of the skin 1102, the bones of the hip 1104, the femur 1110, and an example of a fracture 1106 in the iliac region of the hip 1104.

In a mitigating treatment proximate to the site of the trauma, a first delivery site 1108 can be chosen which can be shaped or sized according to the extent of the trauma, such as a fracture 1106. A first injection guide assembly 1140 can be prepared, having an injector guide 1142 which can be sized and/or shaped to accommodate the size and shape of the first delivery site, which may include being customized according to the patient. The injection guide assembly 1140 also has a plurality guide holes or ports 1144 for directing a needle of an automated injector 820 (FIG. 8B). As described above with reference to FIG. 8B, the automated injector 820 can include an injector needle 822, body 826 and controls 824, and can be operable to deliver a therapeutic dose of a therapeutic agent in one or more aliquots. In various embodiments, the needle 822 is sized to pass through the guide holes 1144 of the first injection guide assembly 1140 in order to deliver the therapeutic agent to the first delivery site 1108. In some embodiments, the injection guide 1142 can also be used in conjunction with a device body, similar to the device body 802 (FIG. 8A-8B) for spacing the injection guide 1142 farther from the skin of a patient, so as to decrease a length of penetration of the injector needle 822.

In a mitigating treatment proximate to a joint near the trauma 1106, a second delivery site 1112 can be chosen, which in some embodiments can be a target region in a muscle mass adjacent to the acetabulofemoral joint, and particularly a region that is impinged by flexure of the joint. A second injection guide assembly 1160 can be prepared and sized and/or shaped to match the second delivery site 1112, and used in conjunction with an automated injector 820 to for delivering the therapeutic agent to the second delivery site, as described above with respect to the first injection guide assembly 1140.

A scanning element 1170 can be applied for scanning one or both of the first and second delivery sites 1108, 1112, e.g., for determining the correct depth of penetration (for customizing or adjusting the injection guides 1140, 1160), or during a procedure to verify the position of an injector needle 822. The scanning element 1170, which can include an ultrasound device or other suitable medical scanner, can be operably connected with a computer system 1172 having a processor and memory 1174, 1176 configured to displace the scanned region at a display 1178.

Figure 12A:
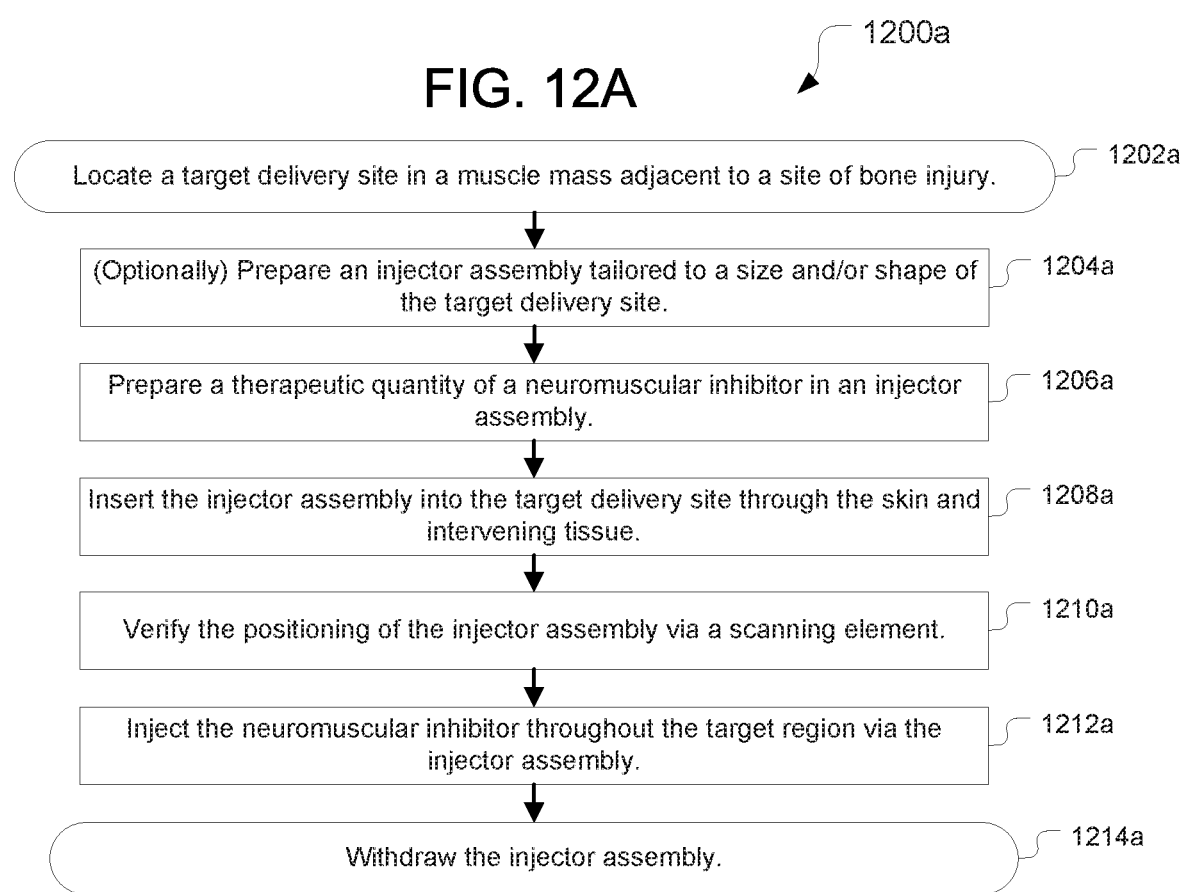
FIG. 12A illustrates treatment of a muscle mass adjacent to a site of bone, nerve or soft tissue injury using a delivery device to inhibit HO formation, according to embodiments.

FIG. 12A illustrates a process 1200a for performing a percutaneous treatment of a region proximate to a site of trauma for preventing HO formation, using a delivery device assembly, according to embodiments. In an embodiment, the process 1200a includes locating a target region in a muscle mass adjacent to a trauma site, i.e. a location of a bone injury such as a hip fracture (act 1202a). In some embodiments, a delivery device assembly 1120 (FIG. 11A) can be tailored or fit according to the size and/or shape of the region adjacent to the fracture (act 1204a). A therapeutic quantity of a neuromuscular inhibitor can be prepared in the delivery device assembly, based on, for example, dosing requirements for inhibition of HO formation, regulatory limitations on the dose size of various particular neuromuscular inhibitors, or other suitable factors (act 1206a). The delivery device assembly can be inserted into the target region through the skin, so that the delivery device assembly penetrates a volume of the target region (act 1208a). In some embodiments, the position of the delivery device assembly relative to the target region can be determined and refined via a scanning element (act 1210a). Then the neuromuscular inhibitor can be injected into the volume of the target region via the delivery device assembly (act 1212a) before it is withdrawn (act 1214a).

Figure 12B:
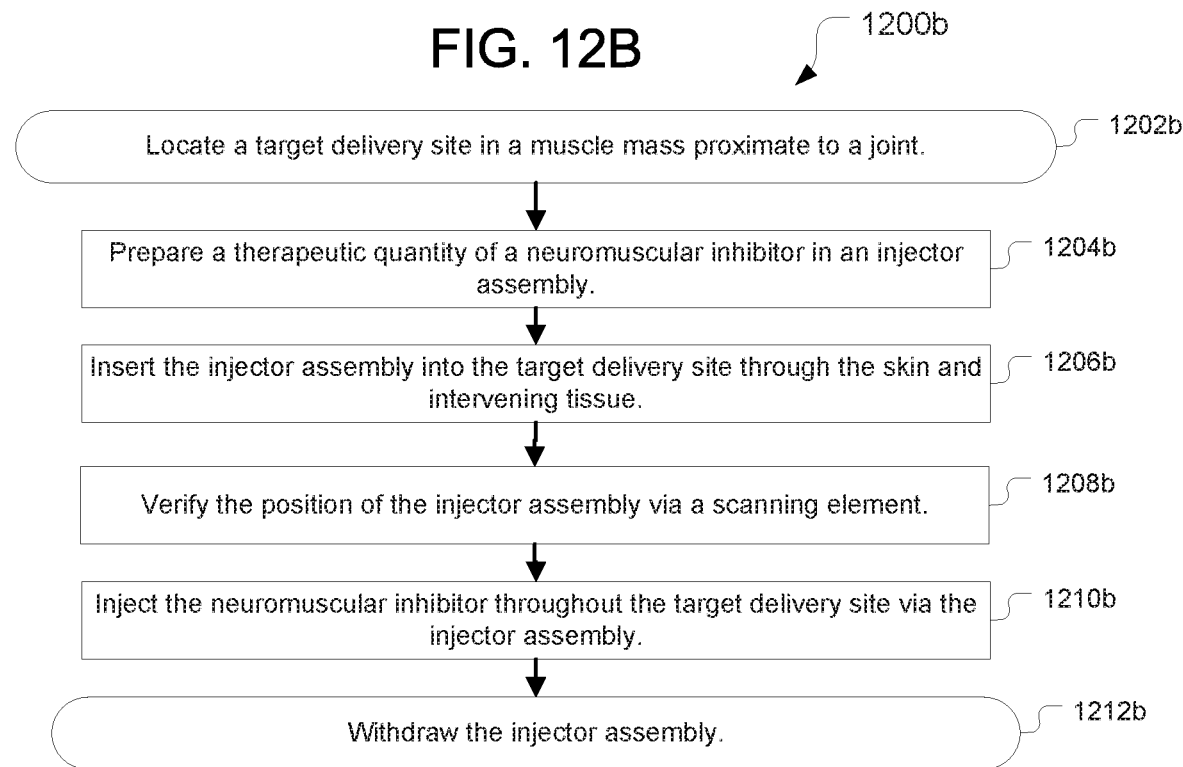
FIG. 12B illustrates a process for performing a mitigating treatment of a muscle mass adjacent to a bone injury using injector assemblies to inhibit HO formation, according to embodiments.

FIG. 12B illustrates a process 1200b for performing a mitigating or preventative treatment of the acetabular region for inhibiting HO formation, using injector assemblies, according to embodiments. In an embodiment, the process 1200b includes locating the target region in a muscle mass adjacent to a site of a joint, such as the acetabulofemoral joint, where the target region is a region impacted by flexure of the joint (act 1202b). A therapeutic quantity of a neuromuscular inhibitor can be prepared in the delivery device assembly (act 1204b), and the delivery device assembly can be inserted into the target region through the skin and intervening tissue (act 1206b). In some embodiments, the position of the delivery device assembly relative to the target region can be determined and refined via a scanning element (act 1208b). Then the neuromuscular inhibitor can be injected into the volume of the target region via the delivery device assembly (act 1210b) before the delivery device assembly is withdrawn (act 1212b).

FIG. 13A illustrates a process 1300a for performing a percutaneous treatment of a region proximate to a site of trauma for preventing HO formation, using an injection guide, according to embodiments. In an embodiment, the process 1300a includes locating a target region in a muscle mass adjacent to a trauma site, e.g. a location of a bone injury such as a hip fracture (act 1302a). In some embodiments, a therapeutic quantity of a neuromuscular inhibitor is prepared based on, for example, dosing requirements for inhibition of HO formation, regulatory limitations on the dose size of various particular neuromuscular inhibitors, or other suitable factors, and loaded in an injector 820 (FIG.

11B) (act 1304*a*). An injection guide, such as injection guide 1140 (FIG. 11B) can be tailored or fit according to the size and/or shape of the region adjacent to the fracture and aligned over the skin with the target region adjacent to the trauma site, such as a hip fracture (act 1306*a*). The automatic injector is inserted into the target region through the skin and via the injection guide, so that the delivery device assembly penetrates a volume of the target region, and an aliquot of the therapeutic agent is delivered to the target region (act 1308*a*). As long as the therapeutic quantity has not yet been injected into all suitable holes or ports of the injection guide (act 1310*a*), a new port is selected for injection (act 1312*a*) and injection of therapeutic aliquots via the injection guide (act 1308*a*) can be repeated. When the therapeutic quantity has been exhausted and/or has been injected through all suitable ports of the injection guide (1310*a*), the injection guide can be removed from the skin above the target region (act 1314*a*). In some embodiments, prior to the first step of injecting the therapeutic aliquot (act 1308*a*), or in some embodiments prior to each step of injecting the aliquot, a scanning element may be used to verify that the guide position and/or depth of penetration of the needle is correct for penetrating the target region (act 1316*a*).

Figure 13B:
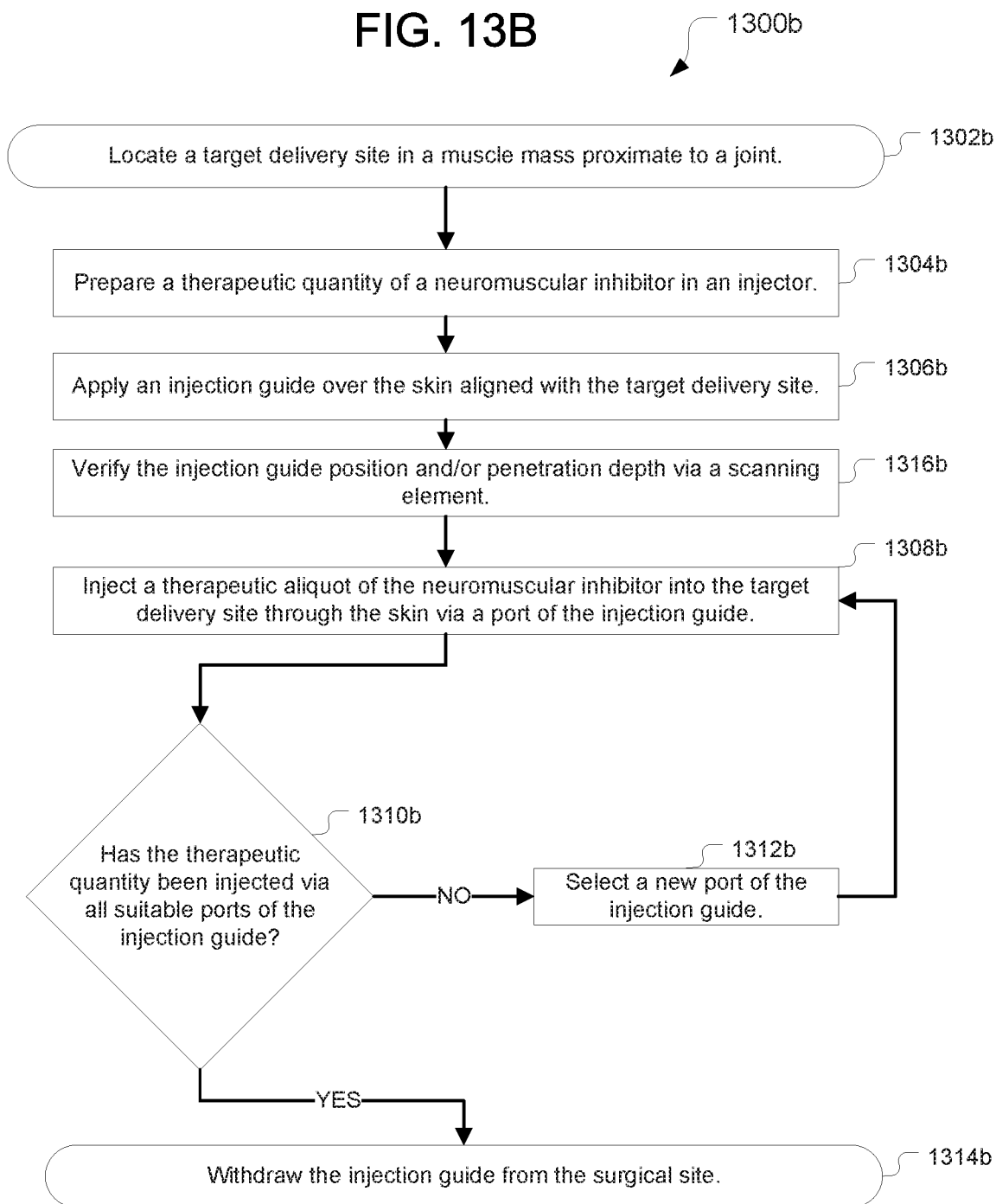
FIG. 13B illustrates a process for performing treatment of a muscle mass proximate to a joint using an injection guide and an automatic injector to inhibit HO formation, according to embodiments.

FIG. 13B illustrates a process 1300*b* for performing a mitigating or preventative treatment of the acetabular region for inhibiting HO formation, using an injection guide, according to embodiments. In an embodiment, the process 1300*a* includes locating a target region in a muscle mass adjacent to a site of a joint, such as the acetabulofemoral joint, where the target region is a region impacted by flexure of the joint (act 1302*b*). In some embodiments, a therapeutic quantity of a neuromuscular inhibitor is prepared based on, for example, dosing requirements for inhibition of HO formation, regulatory limitations on the dose size of various particular neuromuscular inhibitors, or other suitable factors, and loaded in an injector 820 (FIG. 11B) (act 1304*b*). An injection guide, such as injection guide 1160 (FIG. 11B) can be tailored or fit according to the size and/or shape of the target region or physiological parameters of the patient, and aligned over the skin with the target region adjacent to the target region (act 1306*b*). The automatic injector is inserted into the target region through the skin and via the injection guide, so that the delivery device assembly penetrates a volume of the target region, and an aliquot of the therapeutic agent is delivered to the target region (act 1308*b*). As long as the therapeutic quantity has not yet been injected into all suitable holes or ports of the injection guide (act 1310*b*), a new port is selected for injection (act 1312*b*) and injection of therapeutic aliquots via the injection guide (act 1308*b*) can be repeated. When the therapeutic quantity has been exhausted and/or has been injected through all suitable ports of the injection guide (1310*b*), the injection guide can be removed from the skin above the target region (act 1314*b*). In some embodiments, prior to the first step of injecting the therapeutic aliquot (act 1308*b*), or in some embodiments prior to each step of injecting the aliquot, a scanning element may be used to verify that the guide position and/or depth of penetration of the needle is correct for penetrating the target region (act 1316*b*).

Figure 14A:
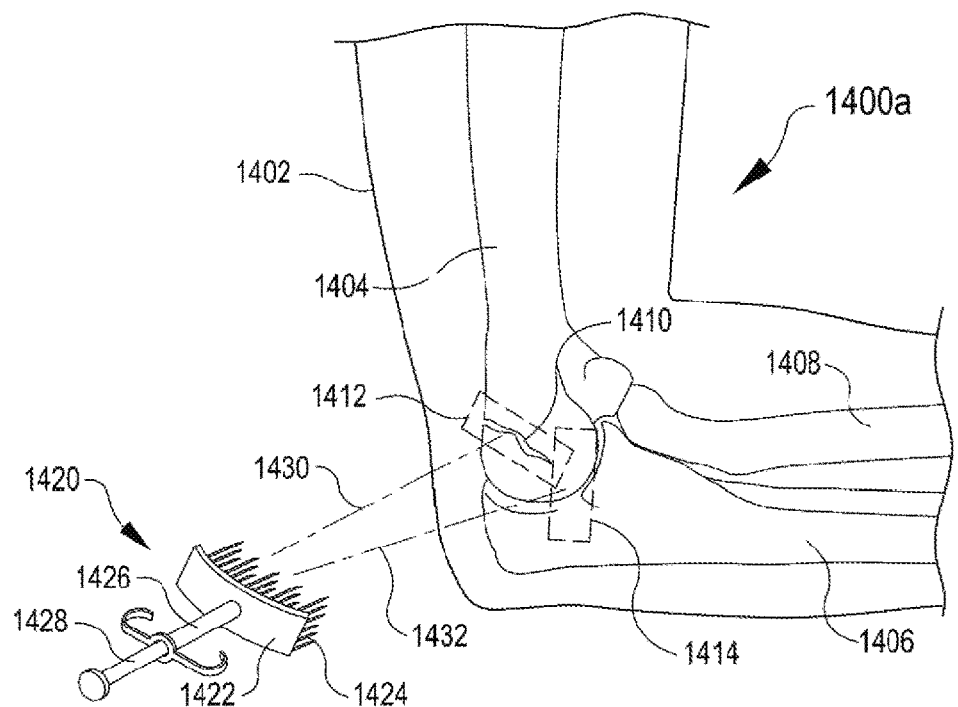
FIG. 14A illustrates protective treatment of the elbow joint using a delivery device to distribute an HO inhibiting agent, according to embodiments.

FIG. 14A illustrates a system 1400*a* for protective treatment of the elbow joint for inhibiting HO formation, using a delivery device assembly, according to embodiments. Shown are approximate locations of the skin 1402, humerus 1404, ulna 1406, radius 1408, and an example trauma site 1410 in the humerus. A first target region 1412 can be selected based on, for example, a region known to be associated with HO lesion formation due to a comparable trauma to the trauma site 1410, or a region proximate to the trauma site. A second target region 1414 can be selected based on, for example, a region which would be impinged by the flexure of a joint, such as the elbow joint, such that preventing the intrusion of an HO lesion into the second target region 1414 would help to preserve mobility of the joint. In some embodiments, a therapeutic quantity of a therapeutic agent, such as a neuromuscular inhibitor, can be prepared in a delivery device 1420, which can be similar to the delivery device assembly 500 (FIG. 5A). The delivery device 1420 can include an injector body 1422 and an array of needles 1424 for delivering a distributed percutaneous dose of the therapeutic agent via the array of needles 1424. In some embodiments, the delivery device 1420 can be operated manually, e.g. via a plunger 1428 and barrel 1426. The protective treatment 1400*a* can include injecting a distributed percutaneous dose of the therapeutic agent to the first target region 1412, to the second target region 1414, or to both regions. The protective treatment 1400*a* may alternatively include injecting a distributed dose intraoperatively through a surgical incision.

Figure 14B:
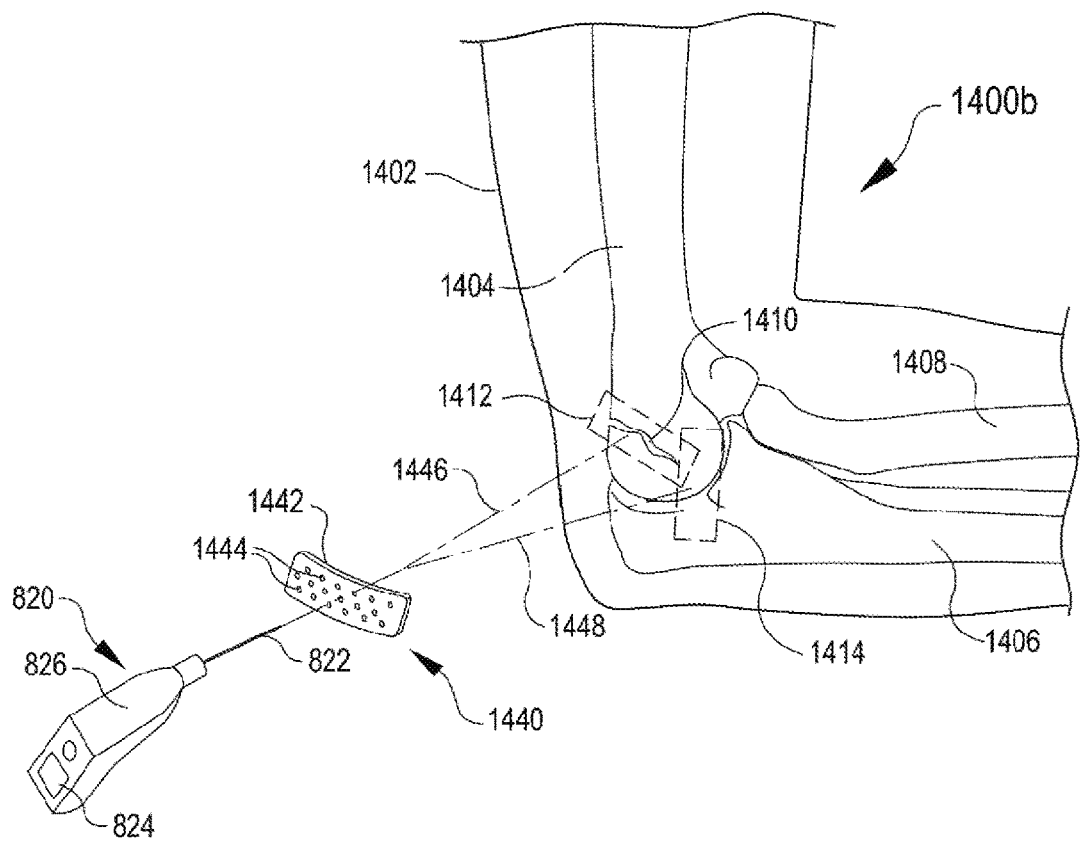
FIG. 14B illustrates protective treatment of the elbow joint using an injection guide and an automatic injector to distribute an HO inhibiting agent, according to embodiments.

FIG. 14B illustrates a system 1400*b* for protective treatment of the elbow joint for inhibiting HO formation, using an injection guide and an automatic injector, according to embodiments. Selection of the first target region 1412 and second target region 1414 can be similar to the selection described above with respect to treatment 1400*a* (FIG. 14A). In some embodiments, a therapeutic quantity of a therapeutic agent, such as a neuromuscular inhibitor, can be prepared in an automatic injector 820, which can include an injector needle 822, body 826, and controls 824. An injection guide 1440 can be applied to the skin 1402 proximate to one or the other, or both, of the of the first and second target regions 1412, 1414. In some embodiments, the injection guide 1440 can be temporarily adhered to the skin 1402, so as to prevent unintended movement of the guide 1440 away from the target regions 1412, 1414. The injector needle 822 of the automatic injector 820 can be inserted through the skin of the patient via the holes 1444 of the injection guide 1440 in order to deliver aliquots of the therapeutic agent throughout one or the other, or both, of the target regions 1412, 1414. The protective treatment 1400*b* can alternatively include injecting a distributed dose intraoperatively through a surgical incision rather than percutaneously.

FIG. 15 illustrates a process 1500 for performing a protective treatment of the elbow joint as shown in FIG. 14A using a delivery device assembly, in accordance with embodiments. In an embodiment, the process 1500 includes locating a target region in a muscle mass adjacent to the trauma site, i.e. a location of a bone injury such as a fracture of the humerus, a location known to be associated with HO lesion formation based on the injury, and/or a location of a muscle mass impinged by motion of the joint located proximate to the trauma site, e.g. a region in the elbow joint proximate to a fracture of the distal humerus (act 1502). In some embodiments, a delivery device assembly 1420 (FIG. 14A) can be tailored or fit according to the size and/or shape of the region adjacent to the fracture (act 1504). A therapeutic quantity of a neuromuscular inhibitor may be prepared in the delivery device assembly, based on, for example, dosing requirements for inhibition of HO formation, regulatory limitations on the dose size of various particular neuromuscular inhibitors, or other suitable factors (act 1506). The delivery device assembly may be inserted into the target region through the skin or intraoperatively through intervening tissue, so that the delivery device assembly penetrates a volume of the target region (act 1508), and then the neuromuscular inhibitor may be injected into the volume of the target region via the delivery device assembly (act 1510) before it may be withdrawn (act 1512).

Figure 16:
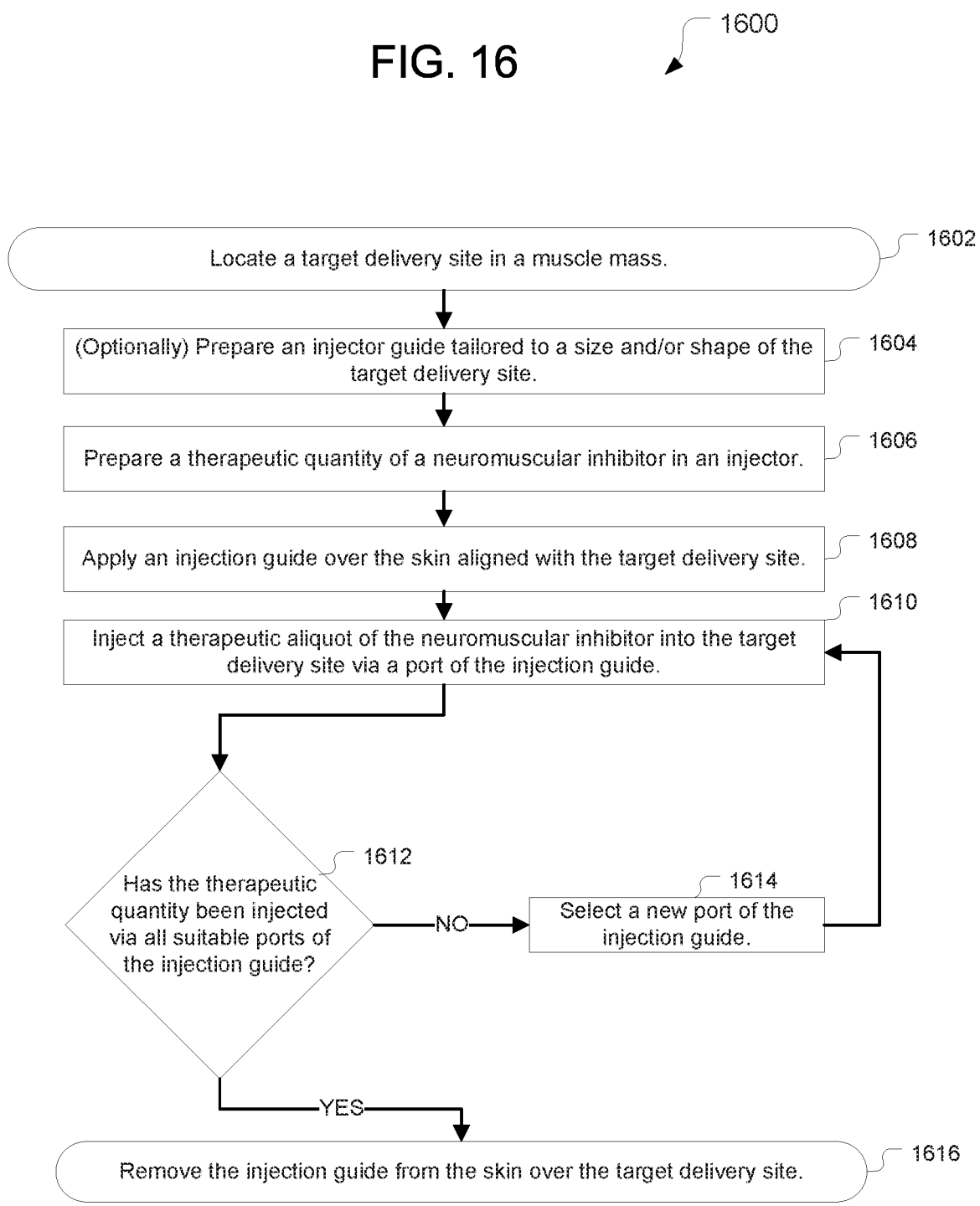
FIG. 16 illustrates a process for performing a protective treatment of a muscle mass using an injection guide and an automatic injector to inhibit HO formation, according to embodiments.

FIG. 16 illustrates a process 1600 for performing a protective treatment of the elbow joint as shown in FIG. 14B using an injection guide and an automatic injector, according to embodiments. In an embodiment, the process 1600 includes locating a target region in a muscle mass adjacent to the trauma site, i.e. a location of a bone injury such as a fracture of the humerus, a location known to be associated with HO lesion formation based on the injury, and/or a location of a muscle mass impinged by motion of the joint located proximate to the trauma site, e.g. a region in the elbow joint proximate to a fracture of the distal humerus (act 1602). In some embodiments, an injection guide such as injection guide 1440 (FIG. 14B) can be tailored or fit according to the size and/or shape of the region adjacent to the fracture and/or the target region in the joint (act 1604). In some embodiments, a therapeutic quantity of a therapeutic agent, such as a neuromuscular inhibitor, can be prepared in an automatic injector such as the automatic injector 820 (FIG. 14B) (act 1606). An injection guide such as the injection guide 1440 (FIG. 14B) can be applied to the skin and may in some embodiments be temporarily adhered to the skin aligned with the target region (act 1608). The injector needle 822 of the automatic injector 820 (FIG. 14B) can be inserted through the skin of the patient via a hole or port of the injection guide in order to deliver an aliquot of the therapeutic agent to the target region (act 1610). As long as the therapeutic quantity has not yet been exhausted or delivered through all suitable ports of the injection guide (act 1612), the aliquot delivery step can be repeated by selecting a new port of the injection guide (act 1614) and injecting additional aliquots of the therapeutic agent via the guide (act 1610). When the target region has been treated by injection of the therapeutic agent through all suitable ports (act 1612), the injection guide can be removed from the skin over the target region (act 1616).

FIG. 17A illustrates a system 1700a for protective treatment of an amputated limb for preventing and/or mitigating HO lesion formation using a delivery device assembly, in accordance with embodiments. Shown are approximate locations of the skin 1702, femur 1704, an amputation region 1706, and a target region 1708. Although described in terms of a treatment of an above-the-knee amputation site, the following embodiments can be applied to any other suitable amputation site. In particular, the following embodiments can help to retain patient comfort and mobility where the formation of an HO lesion could impinge on the comfortable wear and use of a prosthetic device. In embodiments, the target region 1708 can be selected based on, for example, a region known to be associated with HO lesion formation proximate to an amputation site, or a region proximate to or within a region associated with prosthetic wear. In some embodiments, a therapeutic quantity of a therapeutic agent, such as a neuromuscular inhibitor, can be prepared in a delivery device 1720, which can be similar to the delivery device assembly 500 (FIG. 5A). The delivery device 1720 can include an injector body 1722 and an array of needles 1724 for delivering a distributed percutaneous dose of the therapeutic agent via the array of needles 1724. In some embodiments, the delivery device 1720 can be operated manually, e.g. via a plunger 1728 and barrel 1726. The protective treatment 1700a can include injecting a distributed percutaneous dose of the therapeutic agent to the first target region 1708. In some embodiments, the array of needles 1724 can be arranged for delivering a dose intraoperatively rather than percutaneously.

FIG. 17B illustrates a system 1700b for protective treatment of an amputated limb for preventing and/or mitigating HO lesion formation using an injection guide and an automatic injector, in accordance with embodiments. As described above with respect to FIG. 17A, shown are approximate locations of the skin 1702, femur 1704, an amputation region 1706, and a target region 1708, which can be selected in a similar manner to the selection of the target region in treatment 1700a. In some embodiments, a therapeutic quantity of a therapeutic agent, such as a neuromuscular inhibitor, can be prepared in an automatic injector 820 having an injector needle 822, body 826, and controls 824. An injection guide 1730, which can be customized in shape, size, pore count, and or pore distribution, can be applied to the skin proximate to the target region, and may additionally be temporarily adhered to the skin so as to prevent unintended movement of the injection guide 1730 from the target region. The injector needle 822 of the injector guide 820 can be inserted through the skin of the patient via the injection guide 1730 in order to deliver aliquots of the therapeutic agent throughout the target region 1708.

Figure 18:
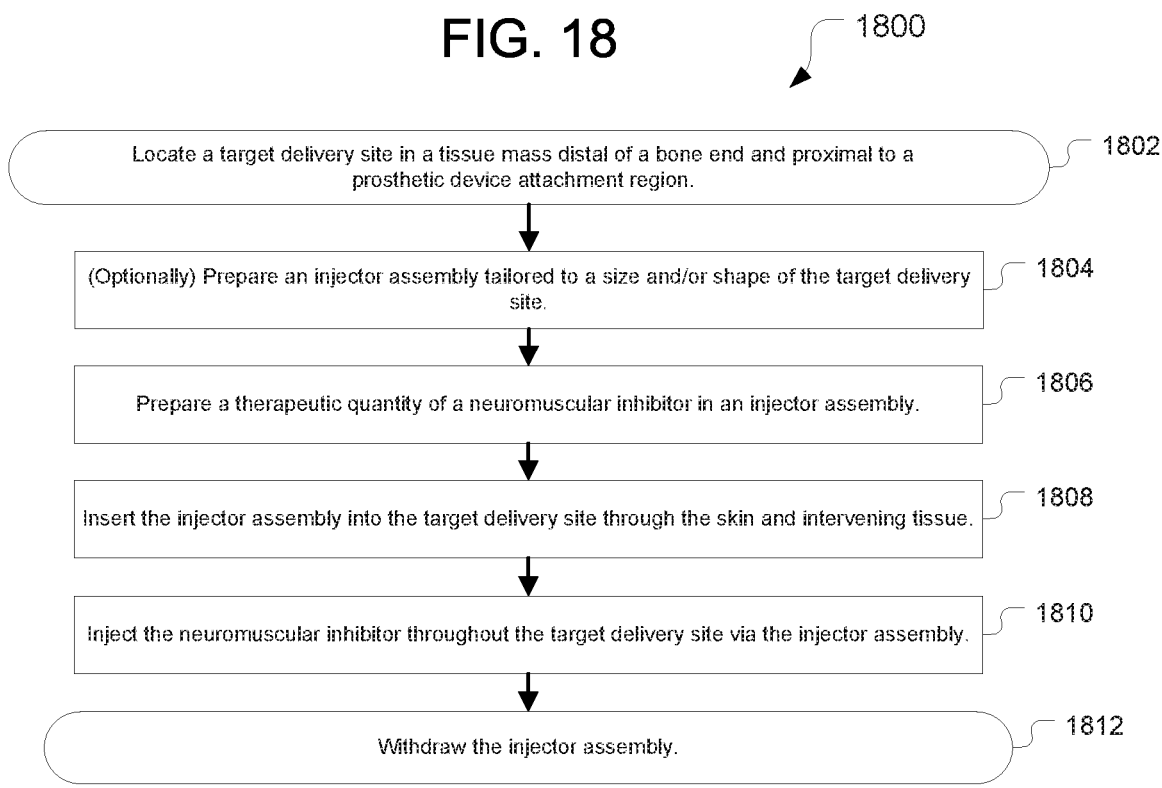
FIG. 18 illustrates a process for performing a protective treatment of an amputated limb using a delivery device assembly to inhibit HO formation, in accordance with embodiments.

FIG. 18 illustrates a process 1800 for performing a protective treatment of an amputated limb using a delivery device assembly, in accordance with embodiments. In some embodiments, the process 1800 includes locating a target region in a tissue mass, such as a muscle, distal of a bone end and proximal to a prosthetic device attachment region (act 1802). In some embodiments, a delivery device assembly 1720 (FIG. 17A) can be tailored or fit according to the size and/or shape of the target region (act 1804). A therapeutic quantity of a neuromuscular inhibitor may be prepared in the delivery device assembly, based on, for example, dosing requirements for inhibition of HO formation, regulatory limitations on the dose size of various particular neuromuscular inhibitors, or other suitable factors (act 1806). The delivery device assembly may be inserted into the target region through the skin, or intraoperatively through intervening tissue, so that the delivery device assembly penetrates a volume of the target region (act 1808), and then the neuromuscular inhibitor may be injected into the volume of the target region via the delivery device assembly (act 1810) before it may be withdrawn (act 1812).

FIG. 19 illustrates a process 1900 for performing a protective treatment of an amputated limb using an injection guide and an automatic injector, according to embodiments. In some embodiments, the process 1900 includes locating a target region in a tissue mass, such as a muscle, distal of a bone end and proximal to a prosthetic device attachment region (act 1902). In some embodiments, an injection guide such as injection guide 1730 (FIG. 17B) can be tailored or fit according to the size and/or shape of the target region (act 1904). In some embodiments, a therapeutic quantity of a therapeutic agent, such as a neuromuscular inhibitor, can be prepared in an automatic injector such as the automatic injector 820 (FIG. 17B) (act 1906). An injection guide such as the injection guide 1730 (FIG. 17B) can be applied to the skin or tissue in a surgical incision. In some embodiments, the injection guide 1730 may be temporarily adhered to the skin aligned with the target region (act 1908). The injector needle 822 of the automatic injector 820 (FIG. 17B) can be inserted through a hole or port of the injection guide in order to deliver an aliquot of the therapeutic agent to the target region (act 1910). As long as the therapeutic quantity has not yet been exhausted or delivered through all suitable ports of the injection guide (act 1912), the aliquot delivery step can be repeated by selecting a new port of the injection guide (act 1914) and injecting additional aliquots of the therapeutic agent via the guide (act 1910). When the target region has been treated by injection of the therapeutic agent through all suitable ports (act 1912), the injection guide can be removed from the skin or tissue over the target region (act 1916).

The methods described above can be implemented using suitable variations of delivery device assemblies, injection guides, and injectors as herein described. For example, FIG. 20 illustrates an alternative embodiment of a delivery device assembly 2000 having an injector body 2002 with an array of needles 2008 with a selection of short and long needles 2010, 2012. In embodiments, the array 2008 with various needle lengths can be used to inject a therapeutic agent into a target volume having a greater depth than might be achieved using needles at a single length. Additionally, plunger-and-barrel (2004, 2006) approach to injecting the therapeutic agent may be substituted for other suitable means of injecting via an array.

FIG. 21 illustrates an example of an alternative embodiment of a delivery device assembly 2100 being attachable with an automatic injector 2110. The automatic injector 2110 can include a body 2114, controls 2116, and a connecting element 2112, which can be any suitable fluid connection; and an injector body 2102 connectable with the automatic injector 2110 via a barrel 2104 and second connecting element 2108. In some embodiments, the automatic injector 2110 can cause a therapeutic agent stored therein to travel through the injector body 2102 and the array of needles 2106. In some other embodiments, a therapeutic quantity of the therapeutic agent can be stored in one or some of the array of needles 2106, injector body 2102, and barrel 2104; and the automatic injector 2110 may, rather than supplied the therapeutic agent, supply mechanical or fluid pressure in order to inject the therapeutic agent via the array of needles 2106.

Figure 22:
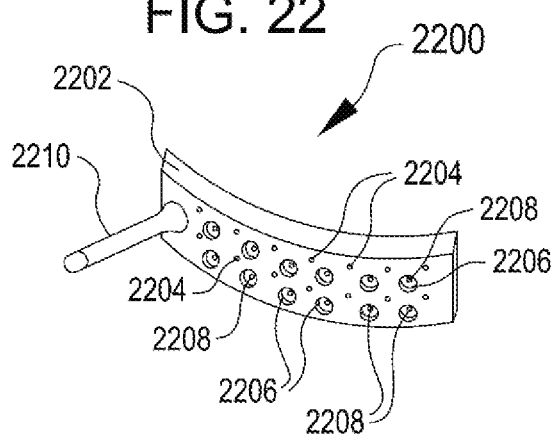
FIG. 22 illustrates an injection guide for accommodating multiple depths of penetration of an injection needle used to distribute an HO inhibiting agent, according to embodiments.

FIG. 22 illustrates an example of an alternative embodiment of an injection guide 2200 for accommodating multiple depths of penetration. In embodiments, the injection guide 2200 can include a guide body 2202, a handle 2210, and a first array of holes 2204 at a first depth, such as a surface, of the guide body 2202. A second array of holes 2208 can be arranged in a set of depressions 2206 in the surface of the guide body 2202. The depressions 2206 can serve to increase a possible penetration depth of an injecting means applied through the holes. In alternative embodiments, additional depths of injection can be accommodated by arranging yet another set of depressions or a set of protrusions that include through-holes in the guide body 2202.

Figure 23:
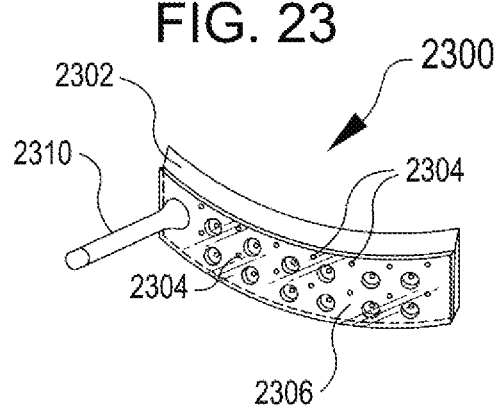
FIG. 23 illustrates an injection guide having a protective film for use in distributing an HO inhibiting agent, according to embodiments.

FIG. 23 illustrates an example of an alternative embodiment of an injection guide 2300 having a protective film. In some embodiments, a protective film or cover 2306 can be applied over the guide body 2302 and holes 2304. The protective film or cover can include an overwrap which may be removable in order to help maintain a sterile surface. In some embodiments, the protective film may further include a layer that remains on the guide body 2302 and can be pierced by an injecting means, such that a practitioner can be further alerted as to which of the holes 2304 have already been used.

In at least some embodiments, the device uses site-specific drug delivery based, at least in part, on the anatomy for each indication. In at least some embodiments, the device: 1) uses targeted delivery of one or more therapeutic agents (e.g., one or more neuromuscular inhibitors) to mitigate heterotopic bone formation; and 2) combines drug dosing parameters with targeted delivery to reduce heterotopic bone formation, while also reducing potential undesired side-effects of the therapeutic agent(s). Use of the device is described herein for acetabular fracture HO inhibition. This is simply one potential embodiment of the device. Additionally, in the case of HO, for example, each different application of the device (e.g., acetabular fracture, amputations, hip arthroplasty, or the like) may utilize a unique device template based on one or more parameters including, for example, anatomy, surgical field, and dosing parameters. Further, each indication may also be subject to different delivery strategies (e.g., a single dose or bolus versus multiple doses versus varying dose volume by location to achieve increased efficacy.

Parameters of the devices and methods described above can be varied without departing from the spirit of the invention. A list of exemplary parameters that may be varied, alone or in combination with other parameters, to promote efficacious treatment of a variety of different anticipated indications include the following.

In selecting the therapeutic agent, a variety of neuromuscular inhibitors may be effective for purposes of inhibiting the formation of HO lesions. For example, the above-described methods may be carried out using any suitable neuromuscular inhibitor. By way of specific example, a suitable neuromuscular inhibitor may include Botulinum toxin type A, Botulinum toxin type B, Abobotulinum toxin A (i.e. Dysport®), Incobotulinum toxinA (i.e. Xeomin®), a combination of any of the above, or other comparable neuromuscular inhibitor.

In another embodiment, the delivery device can be used to target suitable pharmacologic inhibitors of heterotopic ossification to increase efficacy and reduce side effects. Suitable pharmacologic inhibitors include Non-Steroidal Anti-Inflammatory Agents (NSAIDs), COX-2 inhibitors, and/or Nuclear Retinoic Acid Receptor Gamma (RARγ) agonists. It is further understood that the aforementioned neuromuscular and pharmacologic inhibitors of HO may be used singularly or in combination to increase efficacy and reduce side effects.

In the needle arrays, the number, type, length, material, diameter, spatial distribution, length distribution, and orientation can be varied, among other suitable parameters.

Dosing can be varied in at least the following ways. Total dosing amount may be varied, e.g., based on a suitable total dose or a suitable dosing concentration, or both. Dosing may be based on a maximum or a recommended dose according to regulatory standards. A maximum dose may be, for example, approximately 400 units. Dosing may be varied according to muscle size or target delivery site volume. Dosing may be homogenous or heterogeneous among the needles in an array, or among individual delivery sites by an injector via an injection guide. Dosing in an array may be varied across the array, e.g. by varying pressure, concentration, or needle diameter at each needle. Dosing may be varied by type of dosing treatment, e.g. single bolus dosing, continuous dosing, or intermittent dosing. Dosing may be varied according to the dosing route, e.g. percutaneous, intraoperative, preoperative, or arthroscopic. Dosing may be varied by the dosing mechanism, e.g. external pump or manual injection. Dosing may also be varied by varying the dosing rate.

Anatomical targeting can be varied. For example, anatomical a target delivery site can include a volume of tissue, particularly muscle tissue, associated with HO formation. For instance, certain locations may be known to produce HO lesions at a higher rate than other locations based on, for example, patient history or clinical studies. Anatomical targeting can include targeting a site associated with a fracture or proximate to a fracture. Anatomical targeting may also include targeting a site that would be adversely impacted by HO formation. For example, a volume of muscle that is commonly impinged by the flexure of a joint may be a good candidate for a protective inoculation against HO lesion formation according to the above methods. By way of example, the acetabular region, particularly the region impinged by flexure of the hip, may be a candidate for a protective inoculation in response to a fracture either in the acetabular region or even elsewhere in the hip, such as in the iliac region. Anatomical targeting can also include targeting a region associated with impingement by a prosthetic device. By protecting a region associated with an amputated limb from HO lesion formation, a protective procedure may improve the long-term viability of prosthesis use by preventing the development of obstructing HO lesions in the region where the amputated limb interfaces with a prosthetic device.

The delivery device assembly may be formed of a variety of materials. For example, embodiments of a device assembly may be formed of plastic, biocompatible metal, or other suitable materials. Materials used to form a device body can include, for example, various biocompatible plastics, metals, or composite materials. Likewise, materials used to form an injection guide can include various biocompatible plastics, metals, or composite materials. For example, a device body or injection guide may be formed of a compliant and/or flexible polymer. In some cases, a device body or injection guide may be formed of a shapeable polymer, or a soft polymer, suitable for modification or customization by a user. An injector assembly, device body, or injection guide may be customized to be specific to a patient, e.g. by 3D printing a suitable device body 520 (FIGS. 5A-5B) based on specific patient anatomy. In some cases, a suitable injector assembly, device body, and/or injection guide may be selected based on a shoe sizing approach.

Device alignment can be varied. For example, the positioning of an injection assembly or an injection guide may be based directly on an anatomy of the visible surgical field in an intraoperative procedure. The positioning of an injection assembly or injection guide may also, or in the alternative, be based on a detected position of the injection guide or injection needles via a medical imaging system. The positioning of an injection assembly or injection guide may also be based on an approximation of a target delivery site based on other suitable anatomical features. In some cases, the positioning of an injection assembly or injection guide may be varied by the use of a device body for spacing the injection assembly or injection guide away from the skin of the patient, above the target delivery site. In some cases, correct positioning may be confirmed after injection based on, for example, delivery confirmation using radiopaque dyes for percutaneous injections and imaging of drug distribution via the radiopaque dyes within the soft tissue.

As mentioned above, use of a delivery device and/or an injection guide in conjunction with an injector is described herein for treating and/or reducing heterotopic bone formation via one or more targeted injections of one or more neuromuscular inhibitors at, or in proximity to, a region of anticipated HO lesion formation or into a region that would be adversely impacted by HO lesion formation. Various forms of a delivery device other than those herein disclosed may be possible within the scope of the invention, and many other therapeutic agents may be administered using a delivery device for treating many different types of orthopedic conditions.

In at least some embodiments, the device includes a body having a contact surface configured and arranged for placing against patient tissue at an injection location in proximity to a target delivery location. In at least some embodiments, the contact surface is curved. In at least some embodiments, the curvature of the contact surface is shaped to conform to a curvature of at least one patient muscle at an injection location in proximity to the target delivery location. In at least some embodiments, the curvature of the contact surface is shaped to conform to a curvature of at least one patient muscle in proximity to the patient's pelvis. In at least some embodiments, the curvature of the contact surface is shaped to conform to a curvature of at least one muscle at least partially extending at least partially along the patient's leg. In at least some embodiments, the curvature of the contact surface is shaped to conform to a curvature of at least one patient muscle extending between a joint connecting the patient's pelvis and a proximal end of the patient's femur.

In at least some embodiments, a heterotopic-ossification-reducing system includes the device and an injection-control assembly for controlling the depth of tissue penetration of the plurality of needles when the body of the device is positioned against patient tissue at an injection location, the amount of the at least one neuromuscular inhibitor dispensed by the device during an injection, or both. In at least some embodiments, a heterotopic-ossification-reducing system includes the device and a guidance assembly for facilitating guidance of the dispensing ends of the plurality of needles to the target delivery location. In at least some embodiments, the device includes a plurality of needles extending from the body, the plurality of needles in fluid communication with the reservoir. In at least some embodiments, the plurality of needles each include a dispensing end configured and arranged for piercing patient skin and dispensing one or more neuromuscular inhibitors at the target delivery location.

In at least some embodiments, the target delivery location is a region of anticipated heterotopic bone formation located within the patient. In at least some embodiments, the target delivery location is within 4 mm of a region of anticipated heterotopic bone formation. In at least some embodiments, the region of anticipated heterotopic bone formation is a region of the patient's body experiencing, or having previously experienced, at least one of a: spinal cord injury, traumatic brain injury, burn, fracture, muscle contusion, joint arthroplasty, musculoskeletal trauma, amputation following trauma, lower motor neuron disorder, or hereditary disorder. In at least some embodiments, the region of anticipated heterotopic bone formation is a region of the patient's body experiencing, or having previously experienced, a musculoskeletal trauma, such as an acetabular fracture. In at least some embodiments, the region of anticipated heterotopic bone formation is a patient joint connecting the patient's pelvis to a proximal end of the patient's femur.

In at least some embodiments, the injection location is located directly over the target delivery location. In at least some embodiments, the device is configured and arranged to deliver micro and/or nanoliter quantities of one or more neuromuscular inhibitors to the target delivery location. In at least some embodiments, the one or more neuromuscular inhibitors therapeutic treatment includes multiple injections delivered to the target delivery location. In some embodiments, the multiple injections can be delivered along any muscles in proximity to (within 20 cm, 15 cm, 10 cm, 5 cm, 4 cm, 3 cm, 2 cm, 1 cm, 0.7 cm, 0.5 cm, 0.4 cm, 0.3 cm, 0.2 cm, 0.1 cm) the target delivery location.

In at least some embodiments, the device includes a reservoir configured and arranged to receive and temporarily hold at least one neuromuscular inhibitor in an amount suitable for at least one injection into the patient. In at least some embodiments, the device is configured and arranged to deliver quantities of one or more neuromuscular inhibitors to the target delivery location in amounts that are less than amounts used clinically/cosmetically for forehead injections. In at least some embodiments, the patient does not present with spasticity when the device is being used. In at least some embodiments, the patient does not present with spasticity along the muscle over which the device body is positioned at the injection location when the device is being used.

In at least some embodiments, the guidance assembly includes at least one imager, and in at least some embodiments, the injector and/or delivery device assembly interfaces with one or more additional clinical devices.

Figure 24:
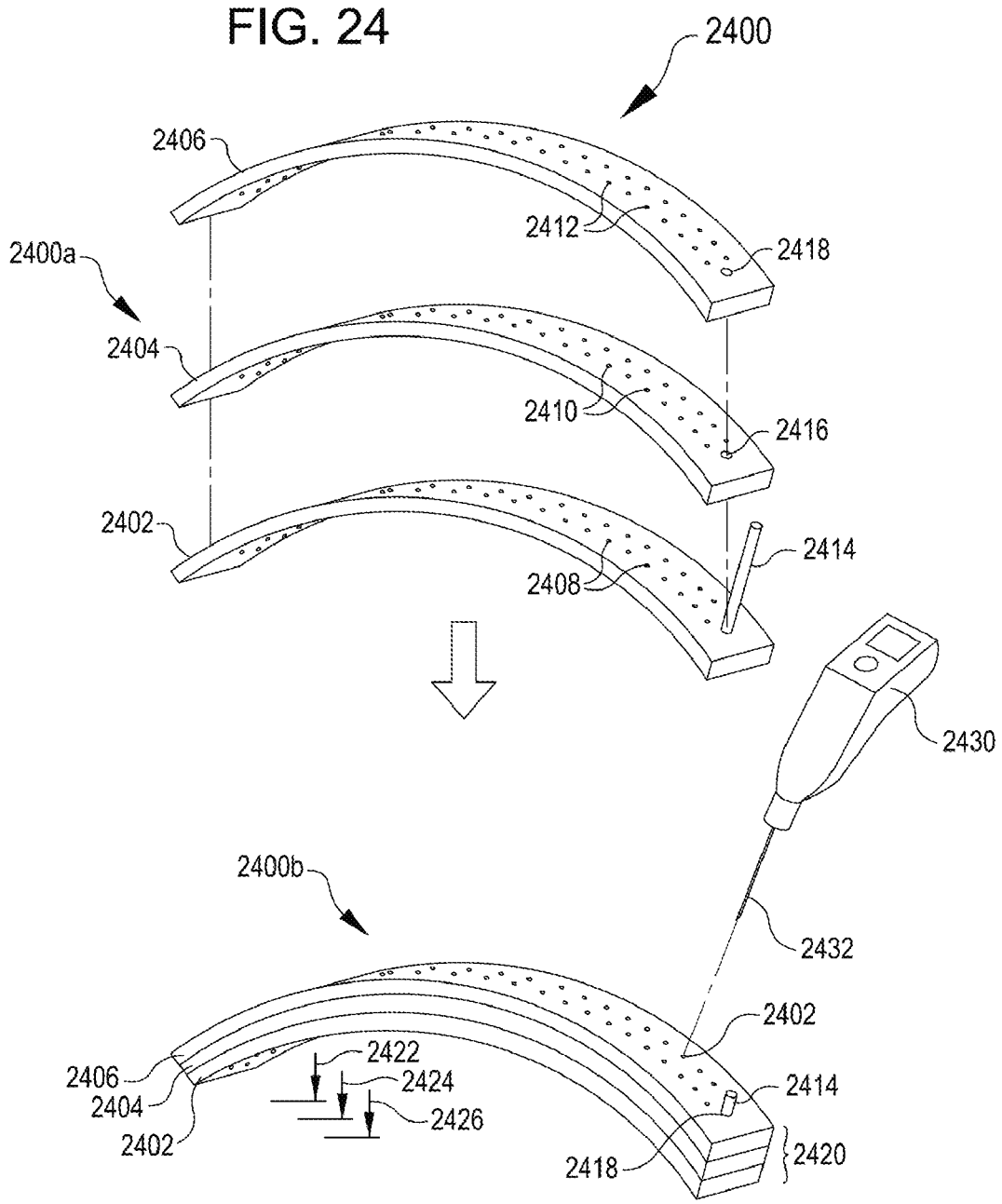
FIG. 24 illustrates an injection guide system for accommodating multiple depths of penetration via multiple guide elements, in accordance with embodiments.

FIG. 24 illustrates an example of an injection guide system 2400 for accommodating multiple depths of penetration via multiple guide elements 2402, 2404, 2406, in accordance with some embodiments. The injection guide system 2400 is shown with reference to an assembly step 2400a, and an assembled configuration 2400b in which the component parts are assembled. The injection guide system 2400 includes a base guide element 2402 which includes an array of holes 2408 sized to accommodate a needle, and optionally a handle 2414 which can be used to position or align the base guide element. Additional guide elements 2404, 2406 are sized to align with the base guide element 2402, and have respective arrays of holes 2410, 2412 which are positioned to align with each other and with the first array of holes 2408 when the guide elements are assembled together. In some embodiments, the additional guide elements 2404, 2406 can include alignment features for aligning the guide elements together and with the base guide element 2402, in order to align the arrays of through-holes 2408, 2410, 2412, such as flanges, mating features, interlocking features, or any other suitable alignment features for linking adjacent parts. For example, in some embodiments, the guide elements 2402, 2404, 2406 can align by way of optional through-holes 2416, 2418 that align with the handle 2414.

In operation, the injection guide system 2400 can be used to provide for stepped injection (e.g., of neuromuscular inhibitor) into an intramuscular target region in a patient at different penetration depths. For example, an injector 2430 or comparable injection means can be used in conjunction with the injection guide system 2400. When assembled, the guide elements 2402, 2404, 2406 form a guide element stack 2420 that limits the depth of penetration possible by a needle 2432 of a given length through the stack. When all guide elements 2402, 2404, 2406 are assembled together, the needle 2432 can penetrate to a first depth 2422. However, as successive guide elements are removed from the stack 2420, the penetration depth of the needle 2432 can be increased, first to a second depth 2424 as the second added guide element 2406 is removed, and finally to a third depth 2426 as the first added guide element 2404 is removed. The example guide system 2400 shown includes a base guide element and two added guide elements 2402, 2404, 2406; however, alternative embodiments may use more or fewer added guide elements in conjunction with a base unit, in order to adjust the depths of penetration of the system or in order to add to or decrease the number of discrete depths. For example, one, two, three, four, or more than four added guide elements may be used in various embodiments to adjust the depth of penetration. Likewise, it may not always be necessary to provide injections at every possible depth of penetration provided by an assembled stack of guide elements. For example, in some cases, one or more added guide elements may be retained permanently on a base guide element during an operation in order to limit the depths of penetration. Generally, when in use, injections will be made by injecting through some or all of the holes in an assembled guide element stack; then removing an added guide element; then injecting again at a greater depth through some or all of the holes in the remaining guide elements; and so on until all guide elements but the base guide element have been removed and injections have been made through the base guide element alone, or until injections have been completed at a maximum depth to which injections are desired. In some cases, injections can be made via the reverse process, in which injections are made through some or all of the holes in a base guide element or minimum assembly of guide elements; followed by adding a guide element; followed by injecting again through some or all of the holes in the assembled guide element stack; and so on until all desired injections have been made at a minimum depth.

Figure 25:
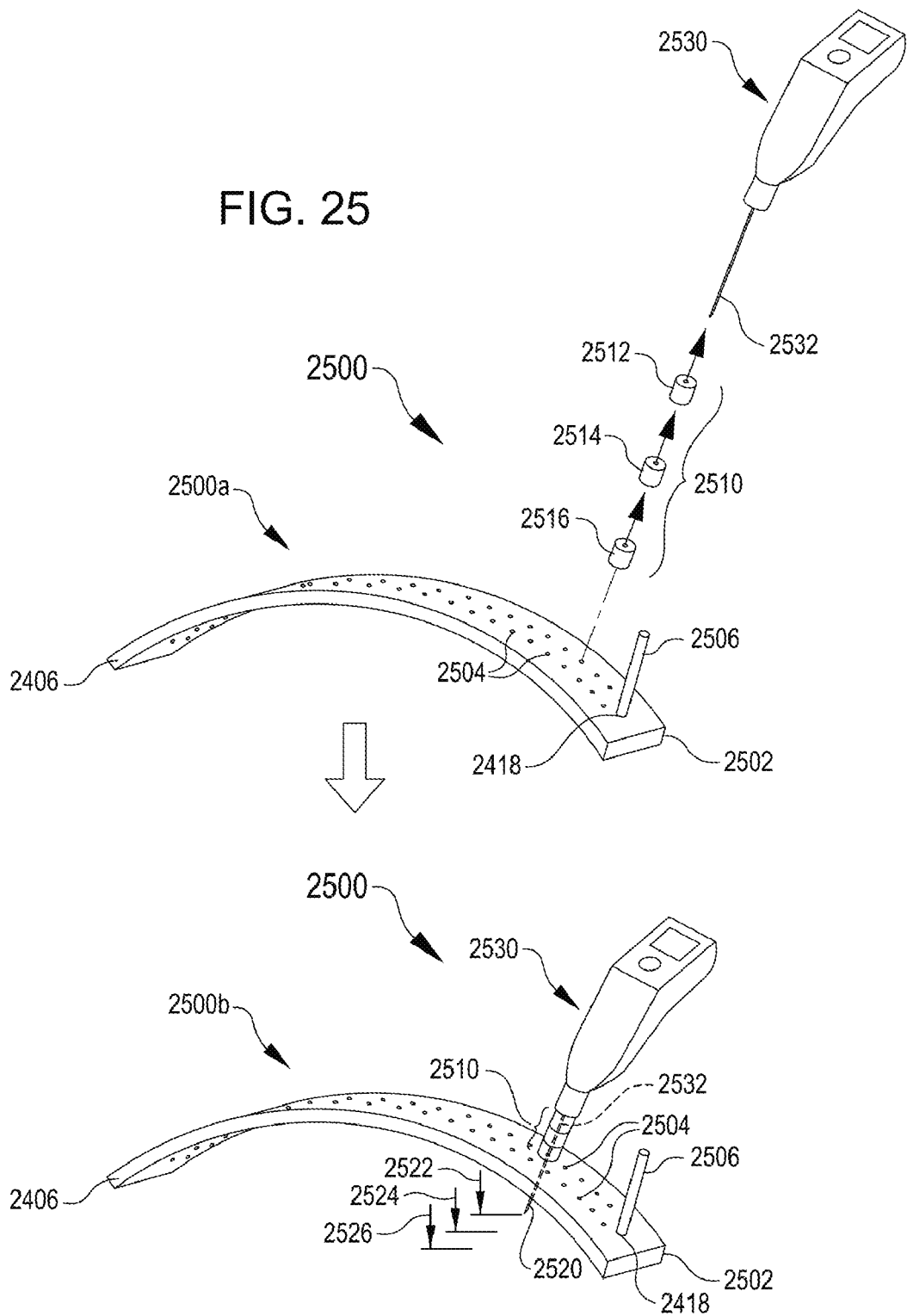
FIG. 25 illustrates an injection guide system for accommodating multiple depths of penetration via multiple spacers in conjunction with a guide element, in accordance with embodiments.

FIG. 25 illustrates an example of an alternative injection guide system 2500 for accommodating multiple depths of penetration via multiple spacers 2512, 2514, 2516, in accordance with some embodiments. The injection guide system 2500 is shown with reference to an assembly step 2500a, and an assembled configuration 2500b in which the component parts are assembled. The injection guide system 2500 includes a guide element 2502 which includes an array of holes 2504 sized to accommodate a needle, and optionally a handle 2506 which can be used to position or align the guide element. Spacers 2512, 2514, 2516, are formed of hollow spacing elements with through-holes sized to accommodate a needle 2532 of an injector 2530 or other comparable injecting means. The spacers 2512, 2514, 2516 can align together to form a spacer stack 2510. In some cases, the spacer stack 2510 can be held together by alignment features for aligning the spacers 2512, 2514, 2516 such as flanges, mating features, interlocking features, or any other suitable alignment features for linking adjacent parts. According to some embodiments, the spacer stack 2510 may be maintained by attaching with the guide 2502, e.g. by suitable mating features positioned at each hole 2504. According to some embodiments, the spacer stack 2510 may be maintained by attaching with the needle 2532 prior to needle insertion through the guide 2502, e.g. by way of connecting together and connecting with the injector 2530; or by way of removably connecting with the needle 2532, e.g. via a mild press fit or similar connection means.

In operation, the injection guide system 2500 can be used to provide for stepped injection (e.g., of neuromuscular inhibitor) into an intramuscular target region in a patient at different penetration depths. For example, the injector 2530 or comparable injection means can be used in conjunction with the injection guide system 2500. According to some embodiments, when assembled, the spacers 2512, 2514, 2516 forming the spacer stack 2510 are connected with either the needle 2532, decreasing the effective length of the needle beyond the stack. When all spacers 2512, 2514, 2516 are assembled together, the needle 2532 can penetrate only to a first depth 2520. However, as successive spacers are removed from the stack 2510, the penetration depth of the needle 2532 can be increased, first to a second depth 2522 as a third spacer 2516 is removed, to a third depth 2524 as a second spacer 2514 is removed, and to a fourth depth 2526 as a first spacer 2512 is removed. The example guide system 2500 shown includes a guide element 2502 and three spacers 2512, 2514, 2516; however, alternative embodiments may use more or fewer spacers in order to adjust the depths of penetration of the system or in order to add to or decrease the number of discrete depths. For example, one, two, three, four, or more than four spacers may be used in various embodiments to adjust the depth of penetration. Likewise, it may not always be necessary to provide injections at every possible depth of penetration provided by an assembled stack of spacers. For example, in some cases, one or more spacers may be retained permanently on a guide element during an operation in order to limit the depths of penetration. Generally, when in use, injections will be made by injecting through some or all of the holes in a guide element; then removing a spacer; then injecting again at a greater depth through some or all of the holes in the guide elements; and so on until all spacers have been removed and injections have been made through the guide element alone, or until injections have been completed at a maximum depth to which injections are desired. In some cases, injections can be made via the reverse process, in which injections are made through some or all of the holes in a guide element alone; followed by adding a spacer; followed by injecting again through some or all of the holes in the guide element at a shallower depth as restricted by the spacer or spacers; and so on until all desired injections have been made.

According to some alternative embodiments, aspects of systems 2400 and 2500 may be used in combination, e.g., by use of multiple guide elements in conjunction with one or more spacers. For example, in at least one embodiment, a maximum injection depth may be established by providing an assembled stack of guide elements and positioning the stack at a delivery site on a patient. Subsequently, a series of injections can be conducted at the maximum depth and at one or more depths that are less than the maximum depth by using one or more spacers to adjust the depth of penetration for delivering a distributed dose, e.g. of neuromuscular inhibitor, throughout a target region in the patient.

In general, embodiments herein disclose apparatuses, systems, and methods for distributing neuromuscular inhibitor as homogenously as possible throughout a volume of interest (VOI) corresponding to a region of a muscle in a patient. The VOI may be a region associated with a high risk of developing HO, a region associated with a high impact in the event that HO develops (e.g. a joint), or a region associated with trauma or other indicator for HO. To that end, embodiments describe apparatuses and methods for performing intramuscular injections in an array, which may be defined by several parameters. For example, parameters affecting the design of an injection array include, but are not limited to, total injection volume, the number of injection sites (i.e., holes or ports in an injection guide, or number of needles in a multi-needle injector), the number of depths and the injection depth of each respective depth, the size and shape of the volume of interest (VOI), and the injected muscle fiber planes within the VOI. To that end, Table 1, below describes examples of some of the above parameters for specific use cases, based on muscle anatomy and certain known, critical soft tissue volumes.

TABLE 1

Select Injection Parameters

| Site of Interest | | VOI volume (cm³) | Number of Injections | Approximate Spacing (cm) |
|---|---|---|---|---|
| Acetabular Fracture/ | min | 100 | 2 | 0.5 |
| Total Hip Replacement | max | 600 | 100 | 5 |
| Elbow Fracture | min | 20 | 2 | 0.25 |
| | max | 100 | 100 | 7.5 |
| Lower Residual Limb | min | 250 | 2 | 0.75 |
| | max | 1000 | 200 | 10 |

As shown in Table 1, above, typical spacing between injection sites suitable for inhibiting HO can range from about 0.25 cm to about 10 cm, depending on the VOI and the specific region of interest. For example, in some embodiments, the spacing between injection sides, and by extension between voids or ports, can be from 0.5 to 5 cm, from 0.25 to 7.5 cm, or from 0.75 to 10 cm. The number of injections in a VOI can vary as well, from as few as 2 injection sites, up to 200 injection sites, or more. For example, in some embodiments, the number of injections can vary from 2 to 100 injections or from 2 to 200 injections. The injections may be planar (i.e., along a single intramuscular plane), or may be spread over multiple injection depths, e.g., at 2-4 injection depths, at 2-5 injection depths, or more. In any case, injection sites are positioned in an intramuscular region, requiring the use of suitable needles or comparable injection means for penetrating into the muscle tissue. To that end, suitable penetration depths may vary from about 0.7 to about 10 cm, in some cases from about 0.5 to about 3 cm, or from 0.5 to 8 cm. Suitable needles for intramuscular penetration are typically greater than 1 mm in length (i.e., longer than conventional micro needles), and are typically defined by needle lengths on the order of 0.25 to 10 cm, or 0.4 to 4 cm.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

What is claimed is:

1. A method of protecting a targeted volume of muscle tissue from heterotopic ossification (HO), the method comprising:
   identifying the targeted volume, within a larger volume of muscle tissue, that is susceptible to HO;
   delivering a first aliquot of a therapeutic dose of a neuromuscular inhibitor at a first delivery site within the targeted volume susceptible to HO; and
   delivering a second aliquot of the therapeutic dose of the neuromuscular inhibitor at a second delivery site within the targeted volume at a first distance from the first delivery, wherein delivering the first and second aliquots separated by the first distance distributes the therapeutic dose within the targeted volume to reduce a required amount of the therapeutic dose for inhibiting HO, such that the therapeutic dose provides a protective concentration of the therapeutic dose that is sufficient to prevent formation of an HO lesion within the targeted volume, but insufficient to induce paralysis of the larger volume of muscle tissue.

2. The method of claim 1, wherein the neuromuscular inhibitor comprises at least one of Botulinum toxin type A, Botulinum toxin type B, Abobotulinum toxin A, or Incobotulinum toxin A.

3. The method of claim 1, wherein the neuromuscular inhibitor comprises at least one of a non-steroidal anti-inflammatory agent (NSAID), a COX-2 inhibitor, or a nuclear retinoic acid receptor gamma (RARγ) agonist.

4. The method of claim 1, further comprising:
   with a delivery device assembly comprising:
      an injector body having a shaped surface configured for complimenting a shape of the muscle volume susceptible to HO; and
      a plurality of needles connected with the injector body and sized to penetrate to an intramuscular depth, wherein the injector body and the plurality of needles are operably connected such that the plurality of needles can distribute injection of the neuromuscular inhibitor into the targeted volume;
   placing the shaped surface of the delivery device assembly against patient tissue proximate to the targeted volume such that dispensing ends of the plurality of needles penetrate through the patient tissue and extend into the targeted volume in at least two locations corresponding to the first and second delivery sites, wherein delivering the first aliquot of the therapeutic dose of the neuromuscular inhibitor comprises ejecting the first aliquot from a first needle of the plurality of needles at the first delivery site, and delivering the second aliquot of the therapeutic dose of the neuromuscular inhibitor comprises ejecting the second aliquot from a second needle of the plurality of needles at the second delivery site.

5. The method of claim 4, further comprising:
   scanning the targeted volume susceptible to HO with a scanning element;
   determining based in part on the scanning, that the plurality of needles is correctly inserted into the targeted volume.

6. The method of claim 1, further comprising:
   with an injection guide having a plurality of guide holes arranged in an array, the injection guide having a shaped guide surface configured for complimenting a shape of the targeted volume susceptible to HO;
   placing the injection guide against patient tissue proximate to the targeted volume;
   inserting a first injection needle through a first guide hole of the injection guide, such that the first injection needle penetrates the targeted volume; and
   inserting a second injection needle through a second guide hole of the injection guide, such that the second injection needle penetrates the muscle volume susceptible to HO targeted volume, wherein:
      delivering the first aliquot comprises ejecting the first aliquot from the first injection needle, and
      delivering the second aliquot comprises ejecting the second aliquot from the second injection needle, wherein the first and second needle can be the same needle or different needles.

7. The method of claim 1, wherein identifying the targeted volume comprises predicting a site where a heterotopic ossification lesion may form in response to a trauma based on a location of the trauma.

8. The method of claim 1, wherein identifying the targeted volume comprises identifying a volume of muscle tissue in a joint where a heterotopic ossification lesion has a likelihood of formation and where the lesion would impinge motion of the flexure of the joint based on a location of the joint or based on a location of a trauma associated with the joint.

9. The method of claim 1, wherein identifying the targeted volume comprises identifying a volume of tissue proximate to an amputated limb, the volume of tissue being at least partially load-bearing when the amputated limb is fitted with a prosthesis.

10. The method of claim 1, wherein:
    the first delivery site and the second delivery site are positioned at respective first and second depths along a single needle path in the targeted volume, the first and second depths being different and separated along the needle path by the first distance; and
    the first and second aliquots are delivered to the first and second delivery sites by sequentially injecting the first aliquot from a needle at the first depth, and injecting the second aliquot from the needle at the second depth.

11. The method of claim 1, further comprising:
with an injection guide having one or more guide holes and a shaped guide surface configured to compliment a shape of a muscle volume susceptible to HO, placing the injection guide against patient tissue proximate to the targeted volume;
placing a spacer adjacent the injection guide and aligned with the one or more guide holes to adjust a relative thickness of the injection guide;
passing a first injection needle through the spacer and the injection guide prior to delivering the first aliquot; and
passing a second injection needle through the injection guide without the spacer prior to delivering the second aliquot.

12. The method of claim 1, further comprising:
aligning an injection guide comprising a body and a plurality of guide holes with the identified target volume;
delivering the first aliquot through a first guide hole of the plurality of guide holes; and
delivering the second aliquot through a second guide hole of the plurality of guide holes that is different from the first guide hole.

13. The method of claim 12, wherein the first aliquot and the second aliquot are delivered simultaneously via first and second needles placed, respectively, through the first and second guide holes.

14. The method of claim 12, wherein the first aliquot and the second aliquot are delivered sequentially via one or more needles placed through the first and second guide holes.

15. The method of claim 12, wherein a first depth of the injection guide at the first guide hole is different from a second depth of the injection guide at the second guide hole, the first and second depths configured to control a penetration depth of a needle passed through either the first guide hole or the second guide hole.

16. The method of claim 1, further comprising delivering a plurality of aliquots of the neuromuscular inhibitor, including the first and second aliquots, the plurality of aliquots being spaced such that the therapeutic dose is distributed evenly throughout the muscle volume.

17. The method of claim 1, wherein the first aliquot is delivered to a first depth and the second aliquot is delivered to a second depth that is different than the first depth.

18. The method of claim 1, further comprising:
delivering the first aliquot and the second aliquot via a needle of an automated injector.

19. The method of claim 1, wherein the therapeutic dose of the neuromuscular inhibitor prevents formation of the HO lesion by local inhibition of neuromuscular function within the targeted volume without inducing paralysis of the larger volume of muscle tissue.

* * * * *